United States Patent
Edgell et al.

(10) Patent No.: US 12,297,467 B2
(45) Date of Patent: *May 13, 2025

(54) LIPID-ENCAPSULATED DUAL-CLEAVING ENDONUCLEASE FOR DNA AND GENE EDITING

(71) Applicant: SPECIFIC BIOLOGICS INC., Toronto (CA)

(72) Inventors: David R. Edgell, London (CA); Thomas A. McMurrough, London (CA); Brent E. Stead, Toronto (CA); Odisho K. Israel, Toronto (CA)

(73) Assignee: SPECIFIC BIOLOGICS INC., Ontario (CA)

( * ) Notice: Subject to any disclaimer, the term of this patent is extended or adjusted under 35 U.S.C. 154(b) by 186 days.

This patent is subject to a terminal disclaimer.

(21) Appl. No.: 17/846,771

(22) Filed: Jun. 22, 2022

(65) Prior Publication Data

US 2023/0016280 A1  Jan. 19, 2023

Related U.S. Application Data

(63) Continuation of application No. 17/514,585, filed on Oct. 29, 2021, which is a continuation of application No. PCT/IB2020/054229, filed on May 4, 2020.

(60) Provisional application No. 62/842,586, filed on May 3, 2019, provisional application No. 63/019,423, filed on May 3, 2020.

(51) Int. Cl.
| | |
|---|---|
| *C12N 9/22* | (2006.01) |
| *A61K 31/7088* | (2006.01) |
| *A61K 38/46* | (2006.01) |
| *C12N 15/11* | (2006.01) |
| *C12N 15/90* | (2006.01) |

(52) U.S. Cl.
CPC ............ *C12N 9/22* (2013.01); *A61K 31/7088* (2013.01); *A61K 38/465* (2013.01); *C12N 15/11* (2013.01); *C12N 15/907* (2013.01); *C12N 2310/20* (2017.05); *C12N 2800/80* (2013.01)

(58) Field of Classification Search
CPC ........ C12N 9/22; C12N 15/11; C12N 15/907; C12N 2310/20; C12N 2800/80; C12N 15/1138; C12N 15/102; A61K 31/7088; A61K 38/465; A61K 9/0043; A61K 38/00; A61K 9/0078; A61K 9/1271; C07K 2319/00; C07K 2319/80; C12R 2001/445

See application file for complete search history.

(56) References Cited

U.S. PATENT DOCUMENTS

| | | | |
|---|---|---|---|
| 8,865,406 B2 | 10/2014 | Zhang et al. | |
| 10,196,651 B2 | 2/2019 | Conway et al. | |
| 11,491,207 B2 | 11/2022 | Khalili et al. | |
| 11,814,658 B2 * | 11/2023 | Edgell | ............... A61K 31/7088 |
| 2022/0195404 A1 * | 6/2022 | Edgell | ..................... C12N 9/22 |
| 2023/0203464 A1 | 6/2023 | Edgell et al. | |
| 2024/0150796 A1 | 5/2024 | Stead et al. | |

FOREIGN PATENT DOCUMENTS

| | | |
|---|---|---|
| WO | WO-2013068845 A2 | 5/2013 |
| WO | WO-2014093622 A2 | 6/2014 |
| WO | WO-2014121222 A1 | 8/2014 |
| WO | 2017049407 A1 | 3/2017 |
| WO | 2017165859 A1 | 9/2017 |
| WO | 2018071868 A1 | 4/2018 |
| WO | 2018136396 A2 | 7/2018 |
| WO | WO-2018237369 A2 | 12/2018 |
| WO | WO-2019060469 A2 | 3/2019 |
| WO | 2020225719 A1 | 11/2020 |

OTHER PUBLICATIONS

Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Guha TK, Edgell DR. Applications of Alternative Nucleases in the Age of CRISPR/Cas9. Int J Mol Sci. Nov. 29, 2017;18(12):2565.
PCT/IB2020/054229 International Preliminary Report on Patentability dated Nov. 2, 2021.
PCT/IB2020/054229 International Search Report and Written Opinion dated Jul. 29, 2020.
Wolfs et al., Biasing genome-editing events toward precise length deletions with an RNA-guided TevCas9 dual nuclease. Proc Natl Acad Sci U S A. Dec. 27, 2016;113(52):14988-14993.
Altschul et al., Basic local alignment search tool. J Mol Biol. Oct. 5, 1990;215(3):403-10. doi: 10.1016/S0022-2836(05)80360-2. PMID: 2231712.
Altschul et al., Gapped BLAST and PSI-BLAST: a new generation of protein database search programs. Nucleic Acids Res. Sep. 1, 1997;25(17):3389-402. doi: 10.1093/nar/25.17.3389. PMID: 9254694; PMCID: PMC146917.
Karlin et al., Applications and statistics for multiple high-scoring segments in molecular sequences. Proc Natl Acad Sci U S A. Jun. 15, 1993;90(12):5873-7. doi: 10.1073/pnas.90.12.5873. PMID: 8390686; PMCID: PMC46825.

(Continued)

*Primary Examiner* — Ganapathirama Raghu
(74) *Attorney, Agent, or Firm* — Mintz, Levin, Cohn, Ferris, Glovsky and Popeo, P.C.

(57) ABSTRACT

Methods to edit genes by administering a chimeric nuclease to a cell or organism without the use of a viral vector.

18 Claims, 7 Drawing Sheets

Specification includes a Sequence Listing.

(56) References Cited

OTHER PUBLICATIONS

Karlin et al., Methods for assessing the statistical significance of molecular sequence features by using general scoring schemes. Proc Natl Acad Sci U S A. Mar. 1990;87(6):2264-8. doi: 10.1073/pnas.87.6.2264. PMID: 2315319; PMCID: PMC53667.

Needleman et al., A general method applicable to the search for similarities in the amino acid sequence of two proteins. J Mol Biol. Mar. 1970;48(3):443-53. doi: 10.1016/0022-2836(70)90057-4. PMID: 5420325.

Pearson et al., Improved tools for biological sequence comparison. Proc Natl Acad Sci U S A. Apr. 1988;85(8):2444-8. doi: 10.1073/pnas.85.8.2444. PMID: 3162770; PMCID: PMC280013.

Smith et al., Comparison of biosequences, Advances in Applied Mathematics, vol. 2, Issue 4, 1981, pp. 482-489, ISSN 0196-8858, https://doi.org/10.1016/0196-8858(81)90046-4.

Wetmur et al., Kinetics of renaturation of DNA. J Mol Biol. Feb. 14, 1968;31(3):349-70. doi: 10.1016/0022-2836(68)90414-2. PMID: 5637197.

Chang et al. (Mar. 19, 2019) "Integrating Combinatorial Lipid Nanoparticle and Chemically Modified Protein for Intracellular Delivery and Genome Editing", Accounts of Chemical Research, 52(3):665-675 (24 pages).

Guha et al. (Nov. 29, 2017) "Applications of Alternative Nucleases in the Age of CRISPR/Cas9", International Journal of Molecular Sciences, 18(12):2565 (13 pages).

Wang et al. (Aug. 20, 2018) "Delivery of the Cas9 or TevCas9 System into Phaeodactylum Tricornutum via Conjugation of Plasmids From a Bacterial Donor", Bio-protocol Journal, 8(16):e2974 (14 pages).

Wishart et al. (Nov. 10, 1995) "A Single Mutation Converts a Novel Phosphotyrosine Binding Domain into a Dual-Specificity Phosphatase", The Journal of Biological Chemistry, 270(45):26782-26785.

Witkowski et al. (Sep. 7, 1999) "Conversion of a Beta-Ketoacyl Synthase to a Malonyl Decarboxylase by Replacement of the Active-Site Cysteine with Glutamine", Biochemistry, 38(36):11643-11650.

Wolfs et al. (Dec. 12, 2016) "Biasing Genome-Editing Events Toward Precise Length Deletions With an Rnaguided Tevcas9 Dual Nuclease", Proceedings of the National Academy of Sciences of the United States of America, 113(52):14988-14993.

International Preliminary Report on Patentability for Application No. PCT/IB2020/054229, mailed on Nov. 9, 2021, 8 pages.

International Search Report and Written Opinion for Application No. PCT/IB2020/054229, mailed on Jul. 29, 2020, 16 pages.

Keskin et al. (2004) "A New, Structurally Nonredundant, Diverse Data Set of Protein-Protein Interfaces and its Implications", Protein Science, 13:1043-1055.

Pakula et al. (1989) "Genetic Analysis of Protein Stability and Function", Anna. Rev. Genet., 23:289-310.

Vakulskas et al. (Aug. 2018) "A High-Fidelity Cas9 Mutant Delivered as a Ribonucleoprotein Complex Enables Efficient Gene Editing in Human Hematopoietic Stem and Progenitor Cells", Nature Medicine, 24(8):1216-1224.

Nishimasu, et al. (Aug. 2015) "Crystal Structure of *Staphylococcus aureus* Cas9", Cell, 162:1113-1126.

Moses, et al. (Mar. 18, 2019) "Applications of CRISPR Systems in Respiratory Health:entering a New 'Red Pen' Era in Genome Editing", Respirology, 24(7):628-637.

* cited by examiner

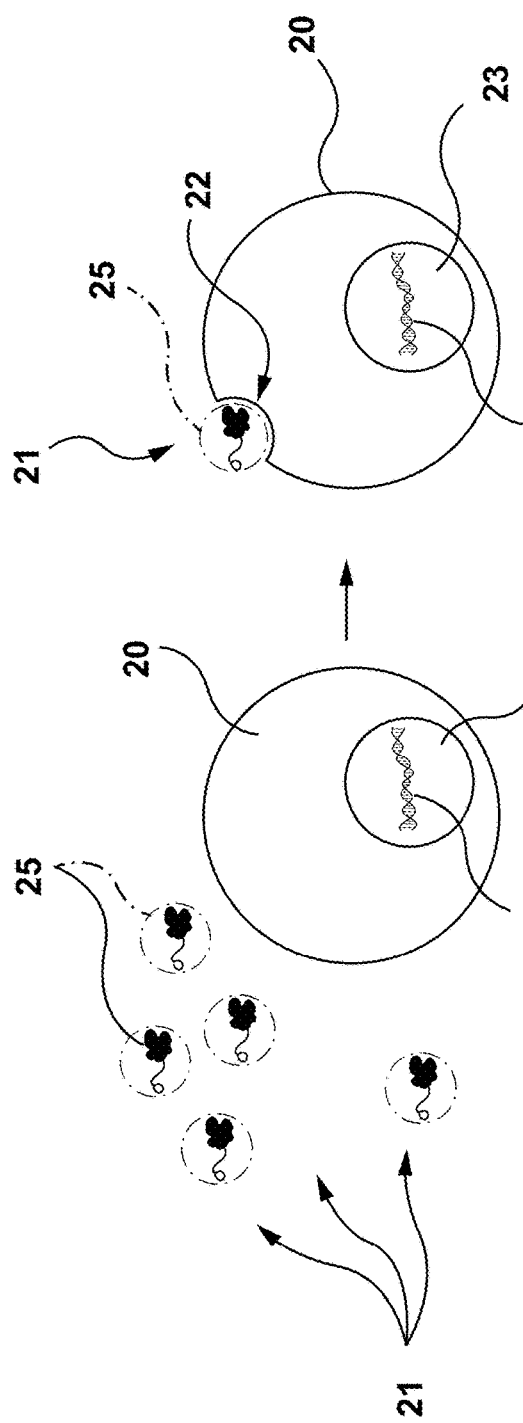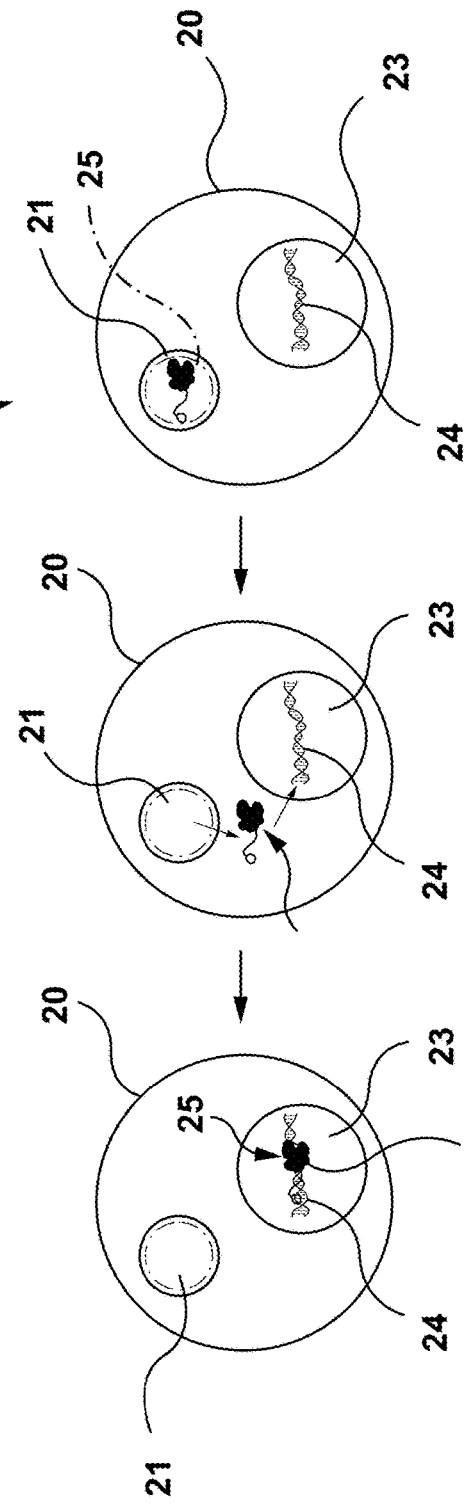

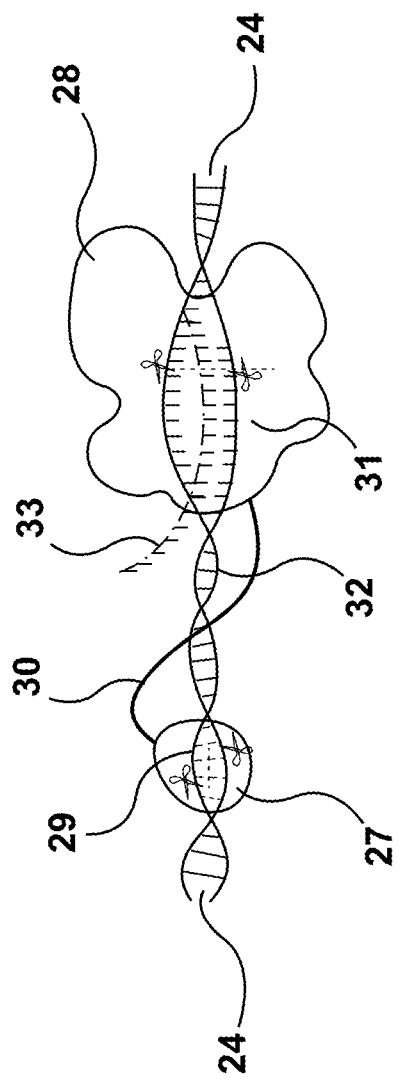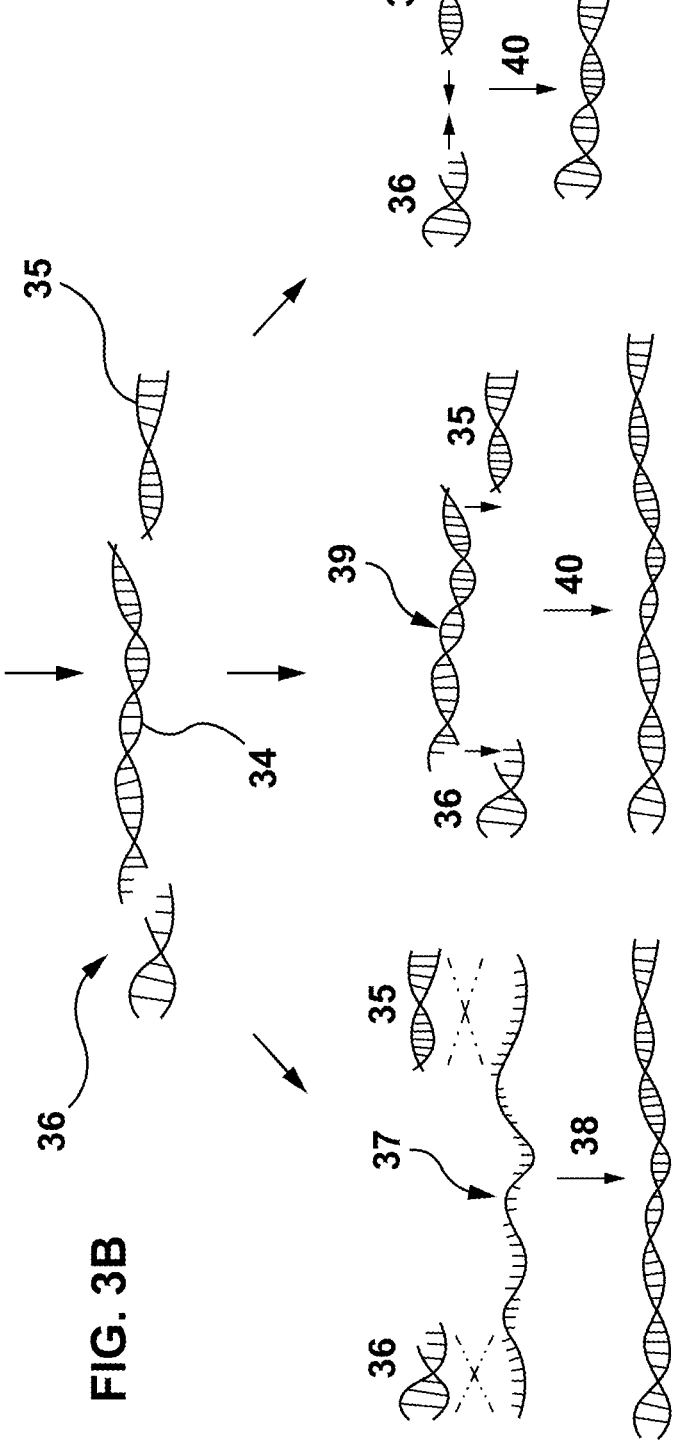

LIPID-ENCAPSULATED DUAL-CLEAVING ENDONUCLEASE FOR DNA AND GENE EDITING

CROSS-REFERENCE

This application is a continuation of U.S. application Ser. No. 17/514,484, filed Oct. 29, 2021, which is a continuation of International application number PCT/IB2020/054229, filed May 4, 2020, which claims benefit of U.S. provisional application No. 62/842,586, filed May 3, 2019, and 63/019,423, filed May 3, 2020, each of which is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Sep. 17, 2018, is Sequence_Listing_ST25.txt and is 77 KB in size.

BACKGROUND OF THE INVENTION

There are an estimated 5,000-10,000 monogenic diseases, defined as inherited conditions arising from mutations on a single gene. These diseases often manifest during childhood and lead to a variety of conditions and sometimes premature death. It has been estimated that together they will affect about 6% of people at some point in their lives. Diagnosis and treatment for these diseases remain largely insufficient, and the care is primarily palliative, focusing on disease management without addressing the underlying genetic defects. There are also many more diseases in which a mutation to a gene contributes to the pathogenesis of the disease.

Gene editing is a gene therapy approach that relies on designer nucleases to recognize and cut specific DNA sequences, and subsequently exploits innate cellular DNA repair pathways, namely nonhomologous end joining (NHEJ) and homology directed repair (HDR), to introduce targeted modifications in the genome. Four nuclease families have been used in this context: meganucleases, zinc-finger nucleases (ZFNs), transcription activator-like effector nucleases (TALENs), and clustered regulatory interspaced short palindromic repeats associated RNA-guided Cas9 (CRISPR-Cas9) nucleases. These can be designed to precisely introduce a double stranded break at the target locus of interest. Gene editing opens up the possibility of permanently modifying a genomic sequence of interest by enabling targeted disruption, insertion, excision, and correction in both ex vivo and in vivo settings. While these advances are expected to revolutionize the field at large, current gene-editing approaches are limited by efficacy of modification, safety concerns related to the specificity of nucleases, and delivery of gene-editing tools to target cell types.

A component of the type II CRISPR system that constitutes the innate immune system of bacteria, the Cas9 (CRISPR-associated) protein has caused a paradigm shift in the field of genome editing due to its ease-of-use. Programming Cas9 to cleave a desired sequence is a simple matter of changing the sequence of the Cas9-associated guide RNA to be complementary to the target site. The ease of programming Cas9 targeting contrasts with the more intensive protein engineering that is required for other reagents (zinc finger nucleases (ZFNs), meganucleases, transcription activator-like effector nucleases (TALENs)). Cas9, along with proteins from type III CRISPR systems have been used for a myriad of genome-editing applications in a diverse range of organisms and are now entering the realm of therapeutic applications in humans.

Cystic fibrosis (CF) is an autosomal-recessive disease resulting from mutations in the CFTR gene, which encodes an epithelial anion channel. The CFTR protein, cystic fibrosis transmembrane conductance regulator, is found across a wide range of organs including pancreas, kidney, liver, lungs, gastrointestinal tracts, and reproductive tracts, making CF a multiorgan disease. Mutations in CFTR lead to suboptimal ion transport and fluid retention, causing the prominent clinical manifestations of abnormal thickening of the mucus in lungs and pancreatic insufficiency. In the lung, dysfunctional CFTR hinders mucociliary clearance, rendering the organ susceptible to bacterial infections and inflammation, ultimately leading to airway occlusion, respiratory failure, and premature death. CF remains the most common and lethal genetic disease among the Caucasian population with 70,000-100,000 sufferers estimated worldwide, highlighting a real need for the development of better treatments.

One major challenge to the development of a therapeutic strategy for CF is the wide diversity of mutation types. Delta F508 (deletion of phenylalanine at codon 508) mutation, with a prevalence of >80% in CF patients, is by far the most common, but more than 1,990 deleterious CFTR-mutations have been described. These mutations cause premature stop codons, aberrant splicing, incorrect protein folding or trafficking to the cell surface, and dysfunctional CFTRs with limited channel-opening capacity. Pharmacological interventions have been targeted to several of these processes and while drug administration is therapeutic in some gating mutation types, the commonly occurring delta F508 still requires a more effective treatment. Pharmaceutical advancement in the care of CF, however, does not address mutations resulting from aberrant splicing or premature stop codons; it is in these instances gene editing could prove most beneficial.

Similarly, in the Western population, approximately 15% of patients with non-small cell lung cancer (NSCLC) harbor an activating mutation in their tumor in the EGF receptor (EGFR) gene.

Existing gene editing technologies, such as CRISPR-Cas9 (and Cas9 fusions), meganucleases, zinc finger proteins, type IIS restriction endonucleases (FokI and FokI fusions) and TALENS are limited in the ability to introduce gene deletions of a specific length or to accurately repair a target gene in a sufficient number of cells to be meaningful as a therapeutic agent for many genetic diseases. Moreover, for highly programmable RNA-guided nucleases, such as the monomeric Cas9, studies suggest that the specificity for predictably binding, cleaving and repairing only their target sites is limited, raising concerns over potential deleterious changes to a cell's genomic DNA that may inadvertently cause a secondary disease in a patient. Last, most nucleases are delivered in viral vectors. Viral vectors have the potential for: existing immunity in many populations; immunogenicity after treatment; and genotoxicity. No non-viral delivery method exists today to safely deliver the nuclease to target cells and allow for controlled dosing of the nuclease in vivo.

There is an unmet need for improvements to said existing gene editing technologies to address the above concerns to make gene editing technologies more efficient and effective.

BRIEF DESCRIPTION OF THE DRAWINGS

FIG. 2A to 2E is a diagram of the mechanism by which lipid-encapsulated TevCas9 is internalized into a cell and nucleus to reach its target DNA. As illustrated in FIG. 2A, a cell 20 or cells 20 are exposed to the novel lipid-encapsulated nuclease particles 21 containing the TevCas9 25 either by in vivo or ex vivo administration. As shown in FIG. 2B, the lipid-encapsulated nuclease particle 21 is endocytosed into the cell 20. The endosome 22 goes through a maturation process in the cytosol and is targeted for degradation (FIG. 2C). On certain occasions, the TevCas9 25 can escape the endosome 22 and enter the cytosol (FIG. 2D). In eukaryotic organisms, the nuclease (TevCas9) 25 is targeted to the nucleus 23 of the cell 20 through one or more nuclear-localization sequences ("NLS"). As depicted in FIG. 2E, through its nuclear localization sequence, TevCas9 25 can enter the nucleus 23 and when in the nucleus 23, the TevCas9 nuclease 25 binds to and cleaves 26 the target genomic DNA 24 sequence.

FIG. 3A to 3E is a diagram of the mechanisms by which lipid-encapsulated TevCas9 modifies target DNA. The I-TevI domain 27 targets the I-TevI Target Sequence 29. The linker domain 30 joins the I-TevI domain 27 with the Cas9 domain 28 which targets the Cas9 Target Sequence 31. The gene mutation 32 is surrounded by or in close proximity to the I-TevI Target Sequence 29 and the Cas9 Target Sequence 31. As shown in FIG. 3B, the TevCas9 25 cleaves the target sequence leaving a deletion product 34 of a predictable size with non-complementary DNA ends 35, 36. FIG. 3C illustrates that in the presence of single-stranded donor DNA with homology arms 37, the cell 20 can insert the donor DNA 37 sequence near the cut sites through the homology-directed repair (HDR) pathway 38. FIG. 3D illustrates that in the presence of donor DNA 39 with compatible DNA ends to those cleaved by TevCas9 25, the cell 20 can insert the donor DNA sequence 39 between the cut sites through directed-ligation using the non-homologous end joining (NHEJ) pathway 40. In the absence of donor DNA, the cell 20 can join the DNA ends through the NHEJ pathway 40 (FIG. 3E).

BRIEF SUMMARY OF THE INVENTION

Figure 1:
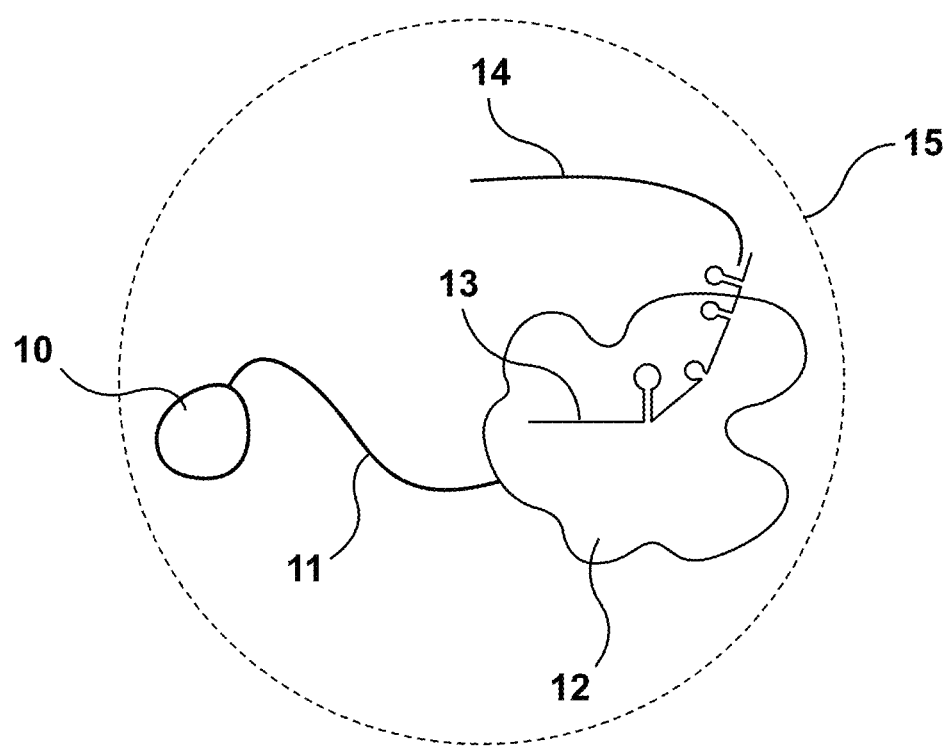
FIG. 1 is a schematic representation of the lipid-encapsulated dual-cleaving nuclease (TevCas9) after it has been prepared [Components are not to scale]. The I-TevI Domain 10 is joined to the RNA-guided Nuclease (Cas9) Domain 12 via a Linker Domain 11. In the preferred embodiment, the formed particles also contain Guide RNA 13 and Donor DNA 14. The aforementioned nuclease is contained in a Lipid Particle 15 which has been shaped into a sphere using an extrusion process.
Figure 4A:
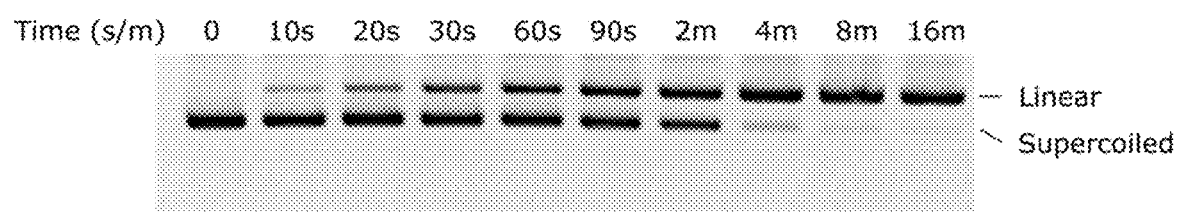
FIG. 4A evidences that TevCas9, targeted to the CFTR gene using guide in SEQ ID 15, cleaves CFTR DNA substrate in vitro.
Figure 4B:
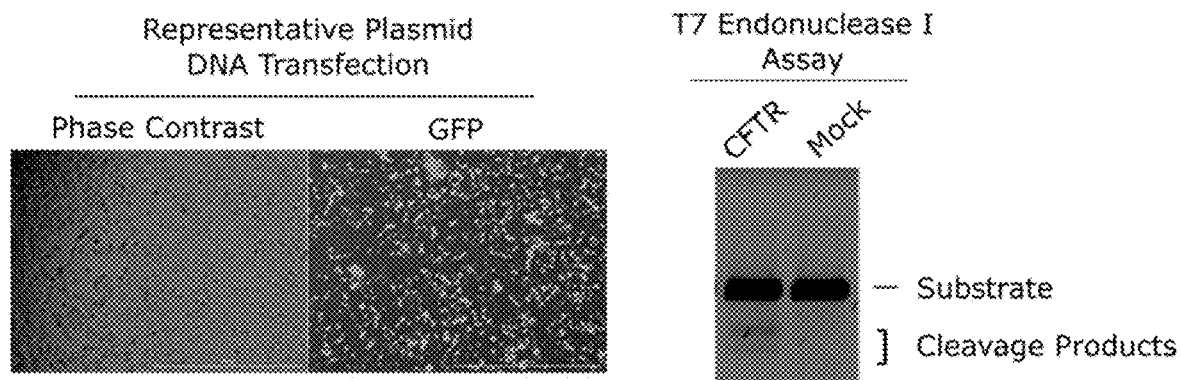
FIG. 4B are cells transfected with a plasmid DNA version of TevCas9 fused to a cleavable GFP tag imaged using phase contrast and GFP imaging on a Cytation5 (Biotek Instruments Inc, VT, USA) after 48 hours treatment. Genomic DNA is extracted from harvested cells and editing at the CFTR gene is detected by PCR amplification and a T7 Endonuclease I cleavage assay.
Figure 5:
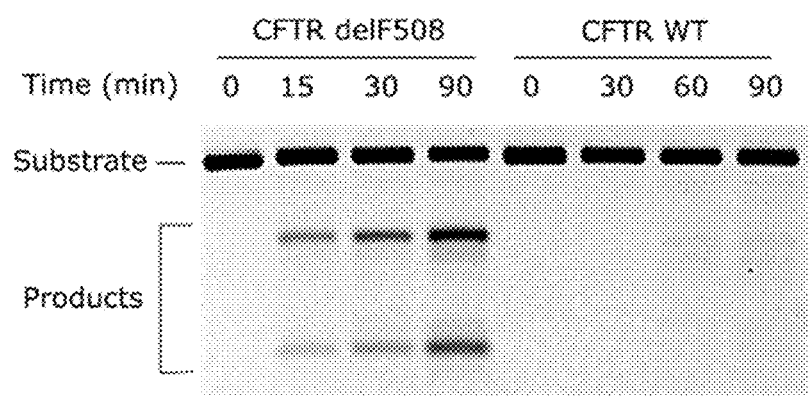
FIG. 5 evidences that TevCas9, targeted to the CFTR Delta F508 mutation using guide in SEQ ID 21, cleaves a DNA substrate containing the CFTR Delta F508 mutation, but not substrate containing the wild-type CFTR sequence in vitro.
Figure 6A:
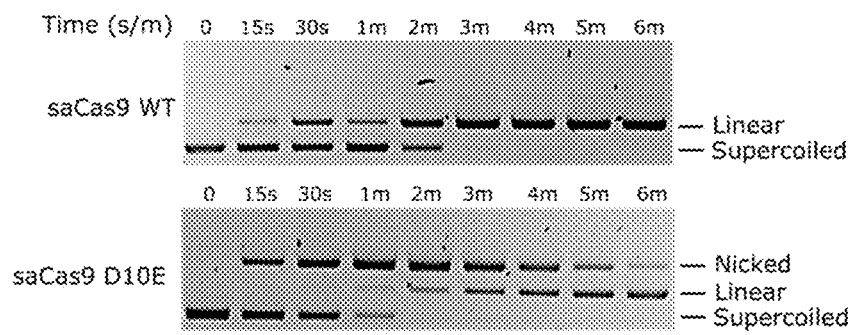
FIG. 6A illustrates that the saCas9 D10E mutation slows the conversion of nicked supercoiled DNA to linear DNA.
Figure 6B:
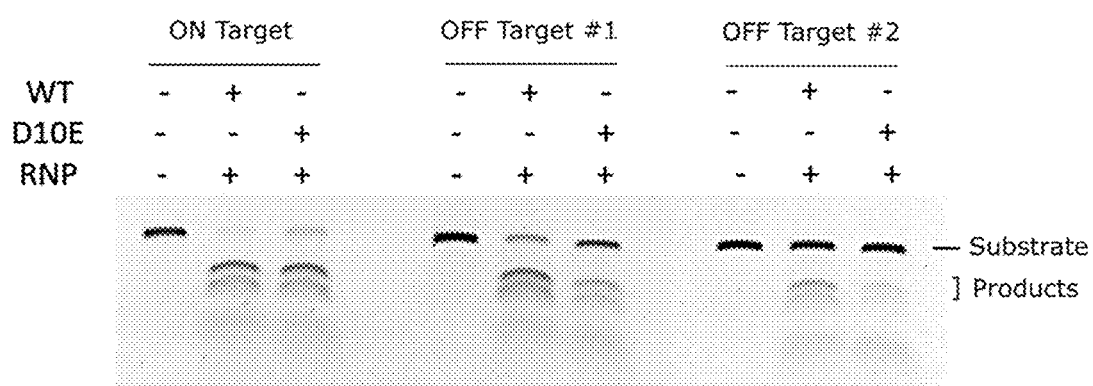
FIG. 6B evidences that on linear EMX1 DNA substrate, saCas9D10E (D10E) ribonucleoprotein complex (RNP) cleaves the target substrate to a similar level as saCas9 wild-type (WT). Levels of editing by SaCas9D10E at computationally predicted off-targets is lower than levels of editing by wild-type saCas9 at the same off-targets.
Figure 7A:
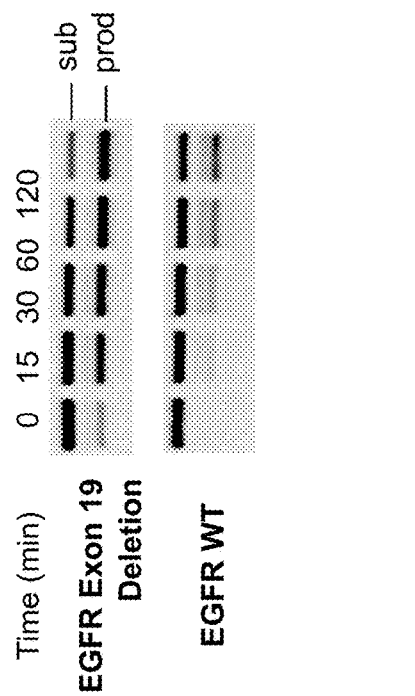
FIG. 7A is a schematic of spacing of the I-TevI sites in the EGFR Exon 19 deletion and wild-type (WT) EGFR.
Figure 7B:
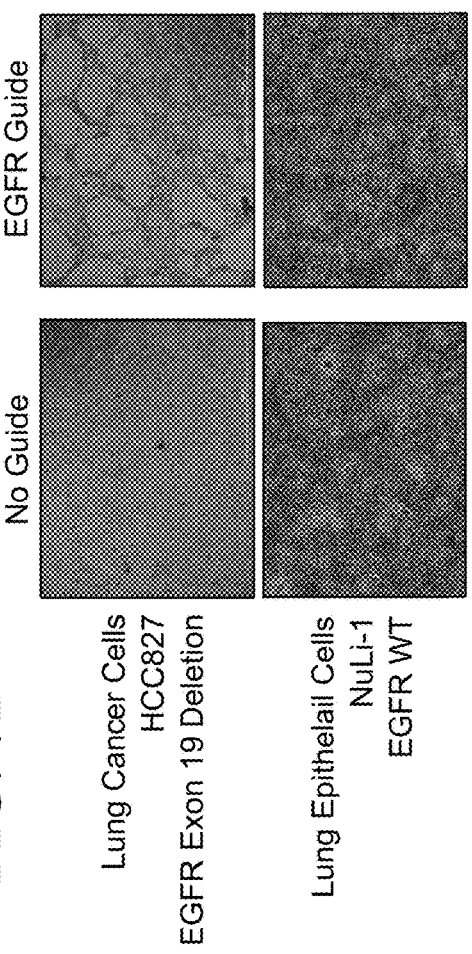
FIGS. 7B and 7C evidences that TevCas9 containing the nicking mutation in Cas9 (H557A) targeted to EGFR using the guide RNA in SEQ ID 16 cleaves EGFR Exon 19 deletion DNA substrate at a 4-fold faster rate than wild type EGFR.
Figure 7C:
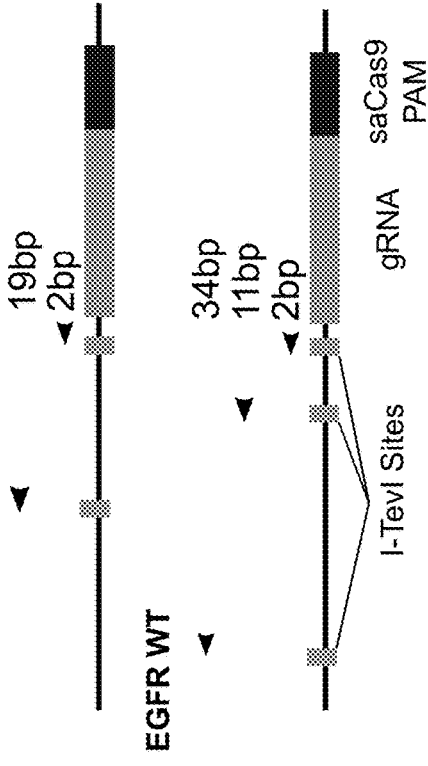
Figure 7D:
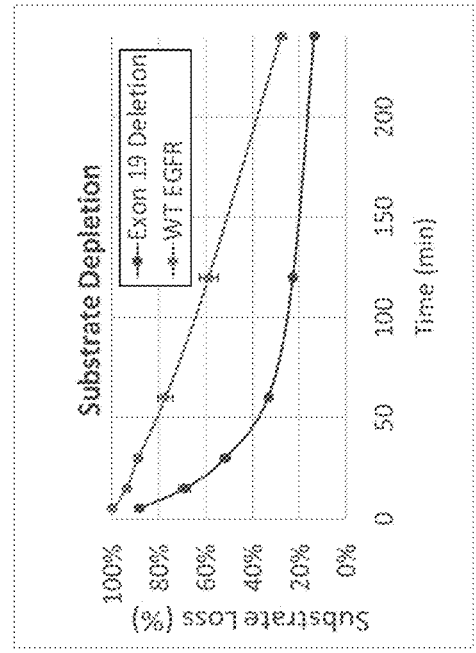
FIG. 7D are images of HCC827 cells harbouring the EGFR Exon 19 deletion mutation treated with TevCas9 targeted to EGFR are selectively killed compared to NuLi-1 cells harbouring wild-type EGFR (WT).

The instant invention is directed to a chimeric nuclease comprising a modified I-TevI nuclease domain, preferably deleting $Met^1$ and having $Lys^{26}$ (which is $Lys^{27}$ in the untruncated version of I-TevI) and/or $Cys^{39}$ (which is $Cys^{41}$ in the untruncated version of I-TevI) modification, a linker, in particular SEQ ID NOS: 7-12 or fragments thereof and/or containing one or more of the following mutations $Thr^{95}$ (as referenced to the full-length I-TevI), $Val^{117}$, $Lys^{135}$, $Gln^{158}$ or $Asn^{140}$, and a modified RNA-guided nuclease *Staphylacoccus aureus* Cas9 that may be the wild-type or a modified version, preferably containing a $Glu^{10}$ or an $Ala^{557}$ mutation thereof wherein said I-TevI polypeptide comprises the entire amino acid sequence of SEQ ID NO: 6 or a fragment thereof, and guide RNA, in particular, SEQ ID NOS: 15, 16 or 21 or fragments thereof, that targets the Cas9 domain and a pharmaceutically-acceptable formulation comprising the chimeric nuclease, cationic and/or neutral lipid nanoparticles, optionally DNA-binding compounds, in particular GL67 ($N^4$-cholesteryl-spermine) and a pharmaceutically acceptable carrier thereof.

In a further embodiment of the instant invention, in the formulation the lipid nanoparticle may contain exogenous donor DNA.

Another embodiment of the invention is directed to methods to edit genes by administering a chimeric nuclease to a cell or organism without the use of a viral vector by using a controlled dose in vivo.

Another embodiment of the invention is directed to methods to delete defined lengths of a DNA molecule or to replace select sequences from a DNA molecule by delivering a chimeric nuclease in vivo to a whole organism or to isolated cells in culture ex vivo wherein said cells are mammalian cells, bacteria, insect cells or plant cells.

In yet another embodiment, the novel chimeric nuclease targets two independent target sites on a select DNA molecule either cleaving at one target site or at both target sites and creating fragments that are 30 to 36 nucleotides in length.

In a further example, the novel, purified chimeric nuclease further comprises a guide RNA.

Another aspect of the instant inventions is the use of an extrusion process creating particles of approximately 100 nM in diameter comprising an excipient wherein the excipient is selected from the group consisting of polysorbates, polyphosphates, calcium chlorides, sodium chloride, sodium citrates, sodium hydroxide, sodium phosphates, sodium ethylenediaminetetraacetic acid, potassium chloride, potassium phosphate and starches, or mixtures of these substances so that the novel chimeric nuclease can be administered to a patient using a nebulizer containing said formulation.

In a preferred embodiment, the instant invention is directed to a method of treating a lung-related disease in a patient in need thereof by administering a novel chimeric nuclease that modifies the DNA of lung epithelial cells wherein the chimeric nuclease replaces the CFTR delta F508 mutation from the CFTR gene in an effort to treat cystic fibrosis or cleaves an EGFR exon 19 deletion in an effort to treat non-small cell lung cancer.

In yet another embodiment, the invention is directed to a chimeric nuclease comprising a modified I-TevI nuclease domain, a linker and a modified RNA-guided nuclease *Staphylacoccus aureus* Cas9 wherein said RNA-guided nuclease *Staphylacoccus aureus* Cas9 contains $Ala^{10}$, $Ala^{557}$ or $Ala^{580}$ mutations and targets the EGFR exon 19 deletions of the EGFR gene.

In a further embodiment, wherein said guide RNA targets a specific CTFR gene sequence to cleave out the CFTR delta F508 mutation or a specific EGFR gene sequence that contains an EGFR exon 19 deletion mutation.

The instant invention also covers linkers comprising SEQ TD NOS: 7-12 or fragments thereof and modified donor DNA molecules selected from the group consisting of a linear single-strand of DNA comprising homologous regions flanking the sites targeted and/or cleaved by a chimeric nuclease, a linear double-strand DNA comprising homologous regions flanking the sites targeted and/or cleaved by a chimeric nuclease, a double strand DNA of the same length comprising complimentary DNA ends to those cleaved by a chimeric nuclease, a circular double-strand DNA comprising homologous regions flanking the sites targeted and/or cleaved by a chimeric nuclease, and a circular double-strand DNA comprising an I-TevI target site and a Cas9 target site wherein the product cleaved from the double-strand DNA contains complimentary ends to the ends cleaved by a chimeric nuclease.

In a further example consists of a chimeric nuclease comprising a modified GIY-YIG nuclease domain, a linker and a modified RNA-guided nuclease *Staphylococcus aureus* Cas9 or *Streptococcus pyogenes* Cas9 or EQR *Streptococcus pyogenes* Cas9 variant containing a $Glu^{10}$ mutation (SEQ ID NO:19) and/or a $Ala^{841}$ mutation and/or a mutation that cleaves the sugar phosphate backbone of a target DNA on one strand of a target DNA wherein said GIY-YIG nuclease domain is selected from the gene family consisting of I-Bmol and Eco29kI.

In yet a further embodiment, the instant invention includes a chimeric nuclease comprising a modified I-TevI nuclease domain, a linker and a modified nuclease or DNA targeting domain wherein said modified nuclease or DNA targeting domain is selected from the group consisting of LAGLIDADG, His-Cys Box, H—N—H, PD-(D/E)×K and Vsr-like meganucleases, zinc-finger nuclease, CRISPR protein selected from the group consisting of scCas9 (*Streptococcus canis*), fnCas9 (*Francisella novicida*), cjCas9 (*Campylobacter jejuni*), Cpf1 (Lachnospiraceae bacterium), Cas12a (Acidaminococcus Sp), Cas13a (*Leptorichia shahii*) and Cas3 (*Streptococcus thermophilus*) and DNA binding domain selected from the group consisting of zinc-finger motifs and TALE activator domains.

In an even further example, the instant invention covers a modified RNA-guided nuclease *Staphylococcus aureus* Cas9 and a guide RNA wherein said guide RNA contains sequences that target genetic polymorphisms, different sequences in the CFTR or EGFR genes, sequences that retarget a nuclease, bridged nucleic acids and/or a mixture of guide RNAs.

DETAILED DESCRIPTION OF THE INVENTION

Definitions and Acronyms

For convenience, certain terms employed in the specification, examples and appended claims are collected here. These definitions should be read in light of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B and C as components.

The term "bioavailable" is art-recognized and refers to a form of the subject disclosure that allows for it, or a portion of the amount administered, to be absorbed by, incorporated to, or otherwise physiologically available to a subject or patient to whom it is administered.

The term "exogenous donor DNA", as used herein, refers to any sequence of DNA that, in whole or in part, is not the same as the original target DNA sequence.

The term "flexible linker", as used herein, refers to a situation when the RNA-guided nuclease domain (Cas9) binds to the target DNA sequence, the amino acid linker domain ensures mobility of the I-TevI domain to allow for recognition, binding and cleaving of its target sequence under cell physiological conditions (typically: pH ~7.2, temperature ~37° C., [K+] ~140 mM, [Na+]~5-15 mM, [Cl−] ~4 mM, [Ca++] ~0.0001 mM). The length of the amino acid linker can influence how many nucleotides are preferred between the Cas9 target site and the I-TevI target site. Certain amino acids in the linker may also make specific contacts with the DNA sequence targeted by TevCas9. These linker-DNA contacts can affect the flexibility of the I-TevI domain. Substituting amino acids in the linker domain may affect the ability of the linker domain to make contact with DNA.

The term "including", as used herein, is used to mean "including but not limited to". "Including" and "including but not limited to" are used interchangeably.

The terms "inhaled administration", "inhale", "inhaled", "inhalation" or "inhalation therapy", which may be used interchangeably and as used herein, include administration of a substantially uniform distribution of appropriately sized particles to the respiratory epithelium of the nose, central airways, the peripheral aspect of the lung and/or the alveolar region of the lung or by intratracheal instillation. Such particles may be introduced to the patient and/or produced using an appropriate device, preferably a nebulizer.

The term "patient," "subject" or "host" to be treated by the subject method may mean either a human or non-human animal. Non-human animals include companion animals (e.g. cats, dogs) and animals raised for consumption (i.e. food animals), such as cows, pigs, and chickens.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as dextrose, lactose, glucose and sucrose; (2) starches, such as corn starch and potato starch; (3) cellulose, and its derivatives, such as microcrystalline cellulose, sodium carboxymethyl cellulose, methyl cellulose, ethyl cellulose, hydroxypropylmethyl cellulose (HPMC), and cellulose acetate; (4) glycols, such as propylene glycol; (5) polyols, such as glycerin, sorbitol, mannitol and polyethylene glycol; (6) esters, such as ethyl oleate, glyceryl behenate and ethyl laurate; (7) buffering agents, such as monobasic and dibasic phosphates, Tris/Borate/EDTA and Tris/Acetate/EDTA (8) pyrogen-free water; (9) isotonic saline; (10) Ringer's solution; (11) ethyl alcohol; (12) phosphate buffer solutions; (13) polysorbates; (14) polyphosphates; and (15) other non-toxic compatible substances employed in pharmaceutical formulations. The disclosed excipients may serve more than one function. For example, a solubilizing agent may also be a suspension aid, an emulsifier, a preservative, and the like.

In certain preferred embodiments, the pharmaceutically acceptable excipient is a crystalline bulking excipient. The terms "crystalline bulking excipient" or "crystalline bulking agent" as used herein means an excipient which provides bulk and structure to the lyophilization cake. These crystalline bulking agents are inert and do not react with the protein or nucleic acid. In addition, the crystalline bulking agents are capable of crystallizing under lyophilization conditions. Examples of suitable crystalline bulking agents include hydrophilic excipients, such as, water soluble polymers; sugars, such as mannitol, sorbitol, xylitol, glucitol, ducitol, inositiol, arabinitol, arabitol, galactitol, iditol, allitol, maltitol, fructose, sorbose, glucose, xylose, trehalose, allose, dextrose, altrose, lactose, glucose, fructose, gulose, idose, galactose, talose, ribose, arabinose, xylose, lyxose, sucrose, maltose, lactose, lactulose, fucose, rhamnose, melezitose, maltotriose, raffinose, altritol, their optically active forms (D- or L-forms) as well as the corresponding racemates; inorganic salts, both mineral and mineral organic, such as, calcium salts, such as the lactate, gluconate, glycerylphosphate, citrate, phosphate monobasic and dibasic, succinate, sulfate and tartrate, as well as the same salts of aluminum and magnesium; carbohydrates, such as, the conventional mono- and di-saccharides as well as the corresponding polyhydric alcohols; proteins, such as, albumin; amino acids, such as glycine; emulsifiable fats and polyvinylpyrrolidone. Preferred crystalline bulking agents are selected from the group consisting of glycine, mannitol, dextran, dextrose, lactose, sucrose, polyvinylpyrrolidone, trehalose, glucose and combinations thereof. Particularly useful bulking agents include dextran.

The term "pharmaceutically-acceptable salts", as used herein, is art-recognized and refers to the relatively non-toxic, inorganic and organic acid addition salts, or inorganic or organic base addition salts of compounds, including, for example, those contained in compositions of the present invention. Some examples of pharmaceutically-acceptable salts include: (1) calcium chlorides; (2) sodium chlorides; (3) sodium citrates; (4) sodium hydroxide; (5) sodium phosphates; (6) sodium ethylenediaminetetraacetic acid; (7) potassium chloride; (8) potassium phosphate; and (9) other non-toxic compatible substances employed in pharmaceutical formulations.

The term "substitution", as used herein, refers to the replacement of an amino acid in a sequence with a different amino acid. As used herein, the shorthand X10Y indicates that amino acid Y has been "substituted" for amino acid X found in the $10^{th}$ position of the sequence. As an example, W26C denotes that amino acid Tryptophan-26 (Trp, W) is changed to a Cysteine (Cys). Similarly, the notation $AA^X$ indicates that AA is an amino acid that replaced the amino acid found in the X position. As an example, $Lys^{26}$ denotes the replacement of the amino acid in the $26^{th}$ position in a sequence with Lysine. Use of either shorthand is interchangeable. In addition, use of the one- or three-letter abbreviations for an amino acid is also interchangeable.

The term "therapeutic agent", as used herein, is art-recognized and refers to any chemical or biochemical moiety that is a biologically, physiologically, or pharmacologically active substance that acts locally or systemically in a subject. Examples of therapeutic agents, also referred to as "drugs", are described in well-known literature references such as the Merck Index, the Physician's Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect", as used herein, is art-recognized and refers to a local or systemic effect in animals, particularly mammals, and more particularly humans caused by a pharmacologically active substance. The term thus means any substance intended for use in the diagnosis, cure, mitigation, treatment, or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "treating", as used herein, includes any effect, e.g., lessening, reducing, modulating, or eliminating, that results in the improvement of the condition, disease, disorder, and the like. As used herein, "treating" can include both prophylactic, and therapeutic treatment. For example, therapeutic treatment can include delaying inhibiting or preventing the progression of cystic fibrosis or non-small cell lung cancer, the reduction or elimination of symptoms associated with cystic fibrosis or non-small cell lung cancer. Prophylactic treatment can include preventing, inhibiting or delaying the onset of cystic fibrosis or non-small cell lung cancer.

As used herein, an "effective amount" refers to an amount sufficient to elicit the desired response. In the present invention, the desired biological response is the treatment of cystic fibrosis and/or non-small cell lung cancer (NSCLC).

A "buffer" as used herein is any acid or salt combination which is pharmaceutically acceptable and capable of maintaining the composition of the present invention within a desired pH range. Buffers in the disclosed compositions maintain the pH in a range of about 2 to about 8.5, about 5.0 to about 8.0, about 6.0 to about 7.5, about 6.5 to about 7.5, or about 6.5. Suitable buffers include, any pharmaceutical acceptable buffer capable of maintaining the above pH ranges, such as, for example, acetate, tartrate phosphate or citrate buffers. In one embodiment, the buffer is a phosphate buffer. In another embodiment the buffer is an acetate buffer. In one embodiment the buffer is disodium hydrogen phosphate, sodium chloride, potassium chloride and potassium phosphate monobasic.

In the disclosed compositions the concentration of buffer is typically in the range of about 0.1 mM to about 1000 mM, about 0.2 mM to about 200 mM, about 0.5 mM to about 50 mM, about 1 mM to about 10 mM or about 6.0 mM.

As used herein, an "anti-microbial agent" is a pharmaceutically acceptable preservative, suitable for administration to a subject, which inhibits, prevents, or delays the growth or microorganisms including, for example bacteria, viruses and fungi in the compositions of the present invention. Suitable anti-microbial agents for use in the compositions and methods of the present invention include, but are not limited to, cresols, benzyl alcohol, phenol, benzalkonium chloride, benzethonium chloride, chlorobutanol, phenylethyl alcohol, methyl paraben, propyl paraben, thiomersal and phenylmercuric nitrate and acetate. In one embodiment the anti-microbial agents is m-cresol, chlorocresol or phenol. In another embodiment the anti-microbial agents is chlorocresol or phenol. In another embodiment the anti-microbial agents is phenol.

As used herein an effective amount of an anti-microbial agent is an amount effective to inhibit, prevent or delay the growth or microorganisms including, for example bacteria, viruses, and fungi in the compositions of the present invention. In the compositions of the present invention, the amount of anti-microbial agent is typically in the range from about 0.1 to about 20 mg/ml, about 0.2 to about 30 mg/ml, about 0.2 to about 10 mg/ml, about 0.25 to about 5 mg/ml, about 0.5 to about 50 mg/ml, about 1 to about 10 mg/ml, about 3 mg/ml or about 5 mg/ml.

The compositions of the present invention can also be lyophilized using lyophilization techniques known in the art and stored as a powder which can be reconstituted prior to administration. The term "lyophilization" as used herein is a freeze drying or dehydration technique which involves removing a solvent, preferably a water miscible solvent, more preferably water from a composition or the present invention, typically by sublimation under high vacuum when the composition is in a frozen state. Typically, lyophilization is carried out in lyophilization equipment (a lyophilizer), which comprises a drying chamber with variable temperature controls, a condenser to collect water, and a vacuum system to reduce the pressure in the drying chamber.

The terms "lyophilized composition", as used herein mean the solid residue or powder which is produced, or which remains after the lyophilization procedure as defined above. The lyophilized composition of the present invention typically further comprises a pharmaceutically acceptable excipient. The term "pharmaceutically acceptable excipient" as used herein refers to a substance which is added to a solution prior to lyophilization to enhance characteristics such as the color, texture, strength, and volume of the lyophilized cake. Pharmaceutically acceptable excipients may be, for example, buffers and pH adjusters, crystalline bulking excipients, stabilizers, and tonicity raising agents.

As used herein, a stabilizer is a composition which maintains the chemical, biological or stability of the chimeric nuclease. Examples of stabilizing agent include polyols, which includes a saccharide, preferably a monosaccharide or disaccharide, e.g., glucose, trehalose, raffinose, or sucrose; a sugar alcohol such as, for example, mannitol, sorbitol or inositol, a polyhydric alcohol such as glycerin or propylene glycol or mixtures thereof and albumin.

A pharmaceutically acceptable salt is a salt which is suitable for administration to a subject, such as, a human. The chimeric nuclease of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like. The chimeric nuclease of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

The above discussion is meant to be illustrative of the principle and various embodiments of the present invention. Numerous variations and modifications will become apparent to those skilled in the art once the above disclosure is fully appreciated. It is intended that the following claims be interpreted to embrace all such variations and modifications.

Abbreviations

Abbreviations used herein are defined as follows:
- AA amino acid
- Cas9 CRISPR-associated protein 9
- CF Cystic fibrosis
- CFTR Cystic fibrosis transmembrane conductance regulator gene
- cjCas9 *Campylobacter jejuni* Cas9
- Cpf1 CRISPR from *Prevotella* and *Francisella* 1
- CRISPR Clustered Regulatory Interspaced Short Palindromic Repeats
- DLS Dynamic Light Scattering
- DMEM Dulbecco's Modified Eagle's Medium
- DMPE 1,2-ditetradecanoyl-sn-glycero-3-phosphoethanolamine
- DNA deoxyribonucleic acid
- DOAB dioctadecyldimethylammonium bromide
- DOPE 1,2-Dioleoyl-sn-glycero-3-phosphoethanolamine
- DPPC Dipalmitoylphosphatidylcholine
- *E. Coli Escherichia coli*
- EDTA ethylenediaminetetraacetic acid
- EGFR Epidermal growth factor receptor
- ELISA Enzyme-linked immunosorbent assay
- fnCas9 *Francisella novicida* Cas9
- HDR Homology directed repair
- IMAC Immobilized Metal Affinity Chromatography
- IPTG Isopropyl β-D-1-thiogalactopyranoside
- MPEG-5000-DMPE N-(carbonyl-methoxypolyethyleneglycol 5000)-1,2 dipalmitoyl-sn-glycero-3-phosphoethanolamine
- NSCLC Non-small cell lung cancer
- NHEJ Non-homologous end joining
- NLS Nuclear-localized signal
- PC Phosphatidylcholine
- PCR polymerase chain reaction
- PE Phosphoethanolamine
- RNA ribonucleic acid
- saCas9 *Staphylococcus aureus* Cas9
- scCas9 *Streptococcus canis* Cas9
- SDS sodium dodecyl sulfate
- spCas9 *Streptococcus pyogenes* Cas9
- TALEN Transcription activator-like effector nucleases
- TEV Tobacco Etch Virus
- TevCas9 Modified I-TevI domain, a linker peptide and modified RNA-guided nuclease *Staphylococcus aureus* Cas9
- ZFN zinc-finger nucleases The Inventors discovered a chimeric nuclease comprising a modified version of an I-TevI domain, a linker peptide and a modified version of an RNA-guided nuclease *Staphylococcus aureus* Cas9 ("saCas9") (hereinafter referred to as "TevCas9") that, when mixed with a lipid nanoparticle, with or without exogenous donor DNA, when delivered to cells, replaces DNA sequences in the presence of exogenous donor DNA or deletes defined lengths of DNA in the absence of exogenous donor DNA. The novel chimeric nuclease has been shown to edit genes in human cells, but also cells of other organisms such as bacteria, yeast, insect, plant, or other mammals, either in whole organisms (in vivo) or in isolated cells cultures (ex vivo).

The novel chimeric nucleases discovered by the present Inventors present the following advantages over existing gene editing technologies and methods, in particular,
a. The nuclease, which is a modified version of the TevCas9 nuclease, is capable of targeting two independent target sites as a single protein and cleaving the DNA at one or both of these sites. It can be reprogrammed to many different target DNA sequences through modifying one or more of the I-TevI domain, the linker domain, the Cas9 domain or the guide RNA (which targets the Cas9 domain to its target sequence);
b. If the nuclease cleaves at two sites, it cleaves out precise lengths of DNA (~30-36 bases depending on the sites targeted by I-TevI and Cas9);
c. The Cas9 domain contains a mutation (D10E) which is rationally designed to modify the Cas9 nuclease activity and/or increase the Cas9 domain's specificity for its target binding site;
d. In the presence of exogenous donor DNA, the invention is designed to replace target DNA sequences in a higher percentage of cells than existing technologies or practices;
e. The nuclease can be purified as a single contiguous protein combined with a guide RNA, which simplifies manufacturing;
f. The lipid nanoparticle allows for non-viral delivery to target cells with high efficiency and low toxicity, allowing for controlled dosing of the nuclease. Although other lipid-based nuclease delivery technologies exist, none are of a composition suitable for use in vivo;
g. The lipid nanoparticles are also designed for the delivery of nuclease through nebulization (inhalation);
h. One version of the nuclease targets and cleaves the CFTR gene to correct the CFTR delta F508 mutation for the treatment of Cystic Fibrosis (SEQ ID NO 1); and
i. Another version of the nuclease is designed to target and cleave the clinically relevant EGFR exon 19 deletion mutations (SEQ ID NOS 2-4), which are present in a variety of cancers, including non-small-cell lung cancer (NSCLC).

The fusion of a GIY-YIG nuclease, such as I-TevI, through a flexible linker to DNA binding domains is known (WO2014/121222). A prior version of the dual-cleaving TevCas9 has been described which comprises amino acids 1-92 of the wild-type I-TevI nuclease domain, a linker region comprising amino acids 93-169 of I-TevI linker region and the *Streptococcus pyogenes* Cas9 ("spCas9") (Wolfs J M et al., (2016), 'Biasing Genome-Editing Events Toward Precise Length Deletions with an RNA-Guided TevCas9 Dual Nuclease,' *Proc Natl Acad Sci USA*, 113(52): 14988-93). The chimeric nuclease of the invention comprises the following:
i. An I-TevI nuclease domain which binds a new target sequence allowing to target clinically relevant gene sequences, such as the CFTR gene;
ii. Various flexible linker regions intended to confer different DNA binding or nuclease activity to TevCas9;
iii. A saCas9 nuclease domain (US-1988/065406 B2). The use of saCas9 over spCas9 results in a smaller DNA coding sequence (~3.7 kilobases for Tev-saCas9 versus ~4.6 kilobases for Tev-spCas9) and lower molecular weight TevCas9 protein (~144 kilodaltons for Tev-saCas9 versus ~179 kilodaltons for Tev-spCas9) which is more amenable to multiple delivery technologies; cleaving by the saCas9 domain between the $3^{rd}$ and $4^{th}$ nucleotide is predictable compared to spCas9 which is more amenable to defined length deletions, as discovered by the inventors of the claimed technology.
iv. One version where the guide RNA is targeted to specific CFTR gene sequence near the CFTR delta F508 mutation; and v. A second version where the guide RNA is targeted to specific EGFR gene sequences and is intended to cleave only DNA with appropriated spaced I-TevI site and Cas9 target site. Such appropriately spaced sites occur in certain EGFR exon 19 deletion mutations (SEQ ID NO 2-4) but not in wild-type EGFR (SEQ ID NO 5);
  a. The invention comprises lipid nanoparticles of certain compositions that are selectively sized to a mean diameter of approximately 100 nM. These lipid nanoparticles are capable of delivering the nuclease to cells with high efficiency and low toxicity;
  b. A pharmaceutical formulation of the lipids, nuclease, and exogenous donor DNA;
  c. A pharmaceutical formulation of the lipids, nuclease and exogenous donor DNA which is suitable for nebulization (inhalation); and
  d. A version of the invention which contains exogenous donor DNA that when delivered with the TevCas9 nuclease in the lipid nanoparticle is capable of integrating into the region between or around the two sites targeted by the nuclease.

The novel chimeric nuclease compositions of the instant application contain different combinations of an I-TevI domain, a linker domain, a Cas9 domain and a guide RNA.

The versions that target the CFTR gene are comprised of:
  i. An I-TevI domain of amino acid sequence according to SEQ ID NO: 6;
  ii. A linker domain according to any one of SEQ ID NOS: 7-12;
  iii. A saCas9 domain of the amino acid sequence according to SEQ ID NO: 13; and
  iv. A guide RNA of the RNA sequence according to SEQ ID NO: 15 or 21.

The versions that target the EGFR gene are comprised of:
  i. An I-TevI domain of amino acid sequence according to SEQ ID NO: 6;
  ii. A linker domain with any one of the amino acid sequences according to SEQ ID NOS: 7-12;
  iii. A saCas9 domain of the amino acid sequence according to SEQ ID NO: 13; and
  iv. A guide RNA of the RNA sequence in SEQ ID NO: 16.

The I-TevI domain of the preferred embodiment is a 93-amino acid I-TevI domain of the Enterobacteria Phage T4 according to the following sequence:

(SEQ ID NO: 6)
MGKSGIYQIKNTLNNKVYVGSAKDFEKRWKRHFKDLEKGCHSSIKLQRS

FNKHGNVFECSILEEIPYEKDLIIERENFWIKELNSKINGYNIA

The saCas9 of the preferred embodiment is a polypeptide comprised of 1,053 amino acids according to the following sequence:

(SEQ ID NO: 13)
MKRNYILGLDIGITSVGYGIIDYETRDVIDAGVRLFKEANVENNEGRRS

KRGARRLKRRRRHRIQRVKKLLFDYNLLTDHSELSGINPYEARVKGLSQ

KLSEEEFSAALLHLAKRRGVHNVNEVEEDTGNELSTKEQISRNSKALEE

KYVAELQLERLKKDGEVRGSINRFKTSDYVKEAKQLLKVQKAYHQLDQS

FIDTYIDLLETRRTYYEGPGEGSPFGWKDIKEWYEMLMGHCTYFPEELR

SVKYAYNADLYNALNDLNNLVITRDENEKLEYYEKFQHIENVFKQKKKP

TLKQIAKEILVNEEDIKGYRVTSTGKPEFTNLKVYHDIKDITARKEIIE

NAELLDQIAKILTIYQSSEDIQEELTNLNSELTQEEIEQISNLKGYTGT

HNLSLKAINLILDELWHTNDNQIAIFNRLKLVPKKVDLSQQKEIPTTLV

DDFILSPVVKRSFIQSIKVINAIIKKYGLPNDIIIELAREKNSKDAQKM

INEMQKRNRQTNERIEEIIRTTGKENAKYLIEKIKLHDMQEGKCLYSLE

AIPLEDLLNNPFNYEVDHIIPRSVSFDNSFNNKVLVKQEENSKKGNRTP

FQYLSSSDSKISYETFKKHILNLAKGKGRISKTKKEYLLEERDINRFSV

QKDFINRNLVDTRYATRGLMNLLRSYFRVNNLDVKVKSINGGFTSFLRR

KWKFKKERNKGYKHHAEDALIIANADFIFKEWKLDKAKKVMENQMFEEK

QAESMPEIETEQEYKEIFITPHQIKHIKDFKDYKYSHRVDKKPNRELIN

DTLYSTRKDDKGNTLIVNNLNGLYDKDNDKLKKLINKSPEKLLMYHHDP

QTYQKLKLIMEQYGDEKNPLYKYYEETGNYLTKYSKKDNGPVIKKIKYY

GNKLNAHLDITDDYPNSRNKVVKLSLKPYRFDVYLDNGVYKFVTVKNLD

VIKKENYYEVNSKCYEEAKKLKKISNQAEFIASFYNNDLIKINGELYRV

IGVNNDLLNRIEVNMIDITYREYLENMNDKRPPRIIKTIASKTQSIKKY

STDILGNLYEVKSKKHPQIIKKG

The saCas9 with a Glu$^{10}$ mutation of the preferred embodiment is a polypeptide comprised of 1,053 amino acids according to the following sequence (the mutation is underlined):

(SEQ ID NO: 14)
MKRNYILGLEIGITSVGYGIIDYETRDVIDAGVRLFKEANVENNEGRRS

KRGARRLKRRRRHRIQRVKKLLFDYNLLTDHSELSGINPYEARVKGLSQ

KLSEEEFSAALLHLAKRRGVHNVNEVEEDTGNELSTKEQISRNSKALEE

KYVAELQLERLKKDGEVRGSINRFKTSDYVKEAKQLLKVQKAYHQLDQS

FIDTYIDLLETRRTYYEGPGEGSPFGWKDIKEWYEMLMGHCTYFPEELR

SVKYAYNADLYNALNDLNNLVITRDENEKLEYYEKFQHIENVFKQKKKP

TLKQIAKEILVNEEDIKGYRVTSTGKPEFTNLKVYHDIKDITARKEIIE

NAELLDQIAKILTIYQSSEDIQEELTNLNSELTQEEIEQISNLKGYTGT

HNLSLKAINLILDELWHTNDNQIAIFNRLKLVPKKVDLSQQKEIPTTLV

DDFILSPVVKRSFIQSIKVINAIIKKYGLPNDIIIELAREKNSKDAQKM

INEMQKRNRQTNERIEEIIRTTGKENAKYLIEKIKLHDMQEGKCLYSLE

AIPLEDLLNNPFNYEVDHIIPRSVSFDNSFNNKVLVKQEENSKKGNRTP

FQYLSSSDSKISYETFKKHILNLAKGKGRISKTKKEYLLEERDINRFSV

QKDFINRNLVDTRYATRGLMNLLRSYFRVNNLDVKVKSINGGFTSFLRR

KWKFKKERNKGYKHHAEDALIIANADFIFKEWKLDKAKKVMENQMFEEK

QAESMPEIETEQEYKEIFITPHQIKHIKDFKDYKYSHRVDKKPNRELIN

DTLYSTRKDDKGNTLIVNNLNGLYDKDNDKLKKLINKSPEKLLMYHHDP

QTYQKLKLIMEQYGDEKNPLYKYYEETGNYLTKYSKKDNGPVIKKIKYY

GNKLNAHLDITDDYPNSRNKVVKLSLKPYRFDVYLDNGVYKFVTVKNLD

VIKKENYYEVNSKCYEEAKKLKKISNQAEFIASFYNNDLIKINGELYRV

-continued

IGVNNDLLNRIEVNMIDITYREYLENMNDKRPPRIIKTIASKTQSIKKY

STDILGNLYEVKSKKHPQIIKKG

The guide RNA of the version that targets the CFTR gene is comprised of 101 ribonucleotides according to the sequences:

(SEQ ID NO: 15)
GCGUCAUCAAAGCAUGCCAACGUUUUAGUACUCUGGAAACAGAAUCUAC

UAAAACAAGGCAAAAUGCCGUGUUUAUCUCGUCAACUUGUUGGCGAGAU

UUU (SEQ ID NO: 21)
AUAUCAUUGGUGUUUCCUAUGGUUUUAGUACUCUGGAAACAGAAUCUAC

UAAAACAAGGCAAAAUGCCGUGUUUAUCUCGUCAACUUGUUGGCGAGAU

UUU

The guide RNA of the version that targets the EGFR gene is 101 ribonucleotides in length according to the following sequence:

(SEQ ID NO: 16)
AAUUUUAACUUUCUCACCUUCGUUUUAGUACUCUGGAAACAGAAUCUAC

UAAAACAAGGCAAAAUGCCGUGUUUAUCUCGUCAACUUGUUGGCGAGAU

UUU.

The linkers used in any of the above constructs may be selected from the group consisting of:

I-TevI domain, linker domain and Cas9 domain. The oligonucleotides are mixed together in blocks of approximately 1 kilobase of the sequence to be synthesized and polymerase chain reaction (PCR) is used to synthesize these ~1 kilobase blocks. The ~1 kilobase blocks are then mixed and subjected to PCR to synthesis the I-TevI domain, linker domain and Cas9 domain. Further, to enhance expression of TevCas9 in *E. coli* and simplify restriction enzyme digestion, the DNA sequence of TevCas9 was optimized prior to synthesis. First, three-base pair DNA codons that are infrequently used by *Escherichia coli* ("*E. coli*") were replaced with those that occur more frequently (for example, of the 6 codons coding for the amino acid arginine, the relative abundance of the codon AGG is 0.03 compared to 0.42 for the codon CGT). In total, 37% of the codons were changed to those preferred by *E. coli*. Second, the content on the nucleotides cytosine and guanine was increased from 39.6% to 48.6%. Third, two *E. coli* ribosome binding sites were removed from the sequence. Fourth, a NdeI restriction endonuclease site was removed from the internal sequence. The contiguous DNA is digested with the restriction endonucleases NdeI and BamHI (New England Biolabs, Ipswich, MA, United States), whose target sites occur only once in the DNA sequence, and then inserted using DNA ligase (New England Biolabs, Ipswich, MA, United States) into a similarly digested pET-11a expression vector (EMD Millipore, Burlington, MA, United States) suitable for expression of TevCas9 in *E. coli*. The pET-11a vector containing TevCas9 is transformed into the *E. coli* expression strain T7 Express (New England Biolabs #C2566, Ipswich, MA, United States) which has been optimized for expression of proteins, including nucleases. Alternatively, the *E. coli* expression

| SEQUENCE (amino acid count) | MUTATION(S) (indicated by underline) | SEQ ID NO: |
|---|---|---|
| DATFGDTCSTHPLKEEIIKKRSETFKAKMLKLGPDGRKALYSKPGSKN GRWNPETHKFCKCGVRIQTSAYTCSKCRNGGSGGS (83 AA) | V117F | 7 |
| DATFGDTCSTHPLKEEIIKKRSETVKAKMLKLGPDGRKALYSRPGSKS GRWNPETHKFCKCGVRIQTSAYTCSKCRNGGSGGS (83 AA) | K135R N140S | 8 |
| DATFGDTCSTHPLKEEIIKKRSETFKAKMLKLGPDGRKALYSRPGSKS GRWNPETHKFCKCGVRIQTSAYTCSKCRNGGSGGS (83 AA) | V117F K135R N140S | 9 |
| DATFGDTCSTHPLKEEIIKKRSETFKAKMLKLGPDGRKALYSRPGSKS GRWNPETHKFCKCGVRIQTSAYTCSKCRGGSGGTGGS (86 AA) | K135R N140S | 10 |
| DATFGDTCSTHPLKEEIIKKRSETFKAKMLKLGPDGRKALYSRPGSKS GRWNPETHKFCKCGVRIQTSAYTCSKCRGGGGSGGGGS (87 AA) | K135R N140S | 11 |
| DATFGDTCSTHPLKEEIIKKRSETFKAKMLKLGPDGRKALYSRPGSKS GRWNPETHKFCKCGVRIQTSAYTCSKCRKESGSVSSEQLAQFRSLD (95 AA) | K135R N140S | 12 |

Synthesis

Example 1: A Method to Manufacture the TevCas9 Nuclease

The DNA coding sequences of the above mentioned I-TevI domain, linker domain and Cas9 domain are synthesized as one contiguous DNA sequence using techniques known in the art. Gene synthesis was conducted by Bio Basic Inc. (Markham, On, Canada). Briefly, short oligonucleotides (~50-60 base pairs) are synthesized which contain regions of overlap to cover the entire sequences of strain BL-21(DE3) (New England Biolabs #C2527, Ipswich, MA, United States) is used. Successful transformations are confirmed by resistance of the *E. coli* to ampicillin or tetracycline and the coding sequence of TevCas9 is verified by DNA sequencing of the expression vector derived from the transformed *E. coli*. The transformed *E. coli* is grown at 37° C. to an optical density of 0.4 to 0.6 as measure by spectrophotometry at a wavelength of 600 nM and the expression of the TevCas9 protein from the pET-11a vector in the transformed *E. coli* expression strain is induced using IPTG for 10-12 hours at 16° C. Successful expression of TevCas9 is verified by the presence of an approximately 150 kDa band on a Coomassie-stained SDS-polyacrylamide gel in a sample of the induced material compared to the uninduced sample. The *E. coli* cells are harvested by centrifugation and resuspended in lysis buffer comprising 10 mM imidazole (Sigma, St. Louis, MO, United States), 300-500 mM sodium chloride (Sigma-Aldrich, St. Louis, MO, United States) and 50 mM sodium phosphate (dibasic) (Sigma, St. Louis, MO, United States), pH 8.0 [Buffer 1]. Alternatively, 10 mM Tris Hydrochloride (Sigma, St. Louis, MO, United States), pH 8 is substituted for substituted for sodium phosphate (dibasic) in Buffer 1. The *E. coli* is lysed by homogenization using a high pressure liquid, homogenizer (Avestin Inc., Ottawa, ON, Canada) operated at 600-1000 bar, or any other suitable lysis method known in the art, such as sonication using a sonifier (Branson Ultrasonics Corp, Danbury, CT, United States) lysozyme treatment, homogenization using a French pressure cell (Glen Mills Inc., Clifton, NJ, United States) or homogenization using a Dounce homogenizer (Corning Inc., Corning, NY, United States). The lysed material is centrifuged at 12,000 rpm at 4° C. for 20-30 mins and the supernatant containing soluble TevCas9 is used for the subsequent purification steps. The pellet contains cell debris, insoluble intracellular material, as well as any insoluble TevCas9. Successful lysis and solubility is verified by the presence of an approximately 150 kDa band on a Coomassie-stained SDS-polyacrylamide gel in a sample of the supernatant when compared to a resuspended sample of the pellet.

The TevCas9 nuclease is purified in the following steps:
1. The lysate containing the nuclease is applied to an immobilized metal affinity chromatography (IMAC) column (GE Healthcare Bio-Sciences AB, Uppsala, Sweden) which binds the nuclease.
2. The IMAC column is washed with Buffer 1.
3. The TevCas9 remaining bound to the column is eluted with a solution comprising 250 mM imidazole (Sigma, St. Louis, MO, United States), 300 mM-500 mM sodium chloride (Sigma-Aldrich, St. Louis, MO, United States) and 50 mM sodium phosphate (dibasic) (Sigma, St. Louis, MO, United States), pH 7.6-8.0 [Buffer 2]. Alternatively, 10 mM Tris Hydrochloride (Sigma, St. Louis MO, United States), pH 7.6-8 is substituted for substituted for sodium phosphate (dibasic) in Buffer 2.
4. The eluate is treated with Tobacco Etch Virus (TEV) protease (New England Biolabs, Ipswich, MA, United States) and incubated with the appropriate guide RNA. The guide RNA is synthesized by Integrated DNA Technology Inc. (Coralville, IA, United States).
5. The treated eluate is re-applied to the IMAC column and the flow-through containing the TevCas9 nuclease and guide RNA is collected.
6. Successful purification of the TevCas9 nuclease is confirmed by the presence of a 150 kilodalton protein band on a Coomassie-stained SDS-polyacrylamide gel. Successful co-purification of TevCas9 with the guide RNA is confirmed by treating a sample of the eluate with Proteinase K (New England Biolabs, Ipswich, MA, United States), then splitting the sample in two and further treating one subsample with RNase A (New England Biolabs, Ipswich, MA, United States) and the other in control buffer without RNase A. A ~100 nucleotide RNA band will be visible on an urea-polyacrylamide gel in the control sample and will be absent in the RNase A-treated sample.
7. The solution containing the TevCas9 nuclease and guide RNA is dialyzed into a solution comprising phosphate buffered saline, pH 7.4.

Example 2: A Method to Manufacture the Lipid Nanoparticles

The lipid nanoparticles of the preferred embodiment are comprised of one of the following mixtures:
I. Lipid nanoparticle No. 1 comprises DOPE (Avanti Polar Lipids, Alabaster, AL, United States) and MPEG-5000-DMPE (Avanti Polar Lipids, Alabaster, AL, United States) in a molar ratio of 2:0.05, respectively;
II. Lipid nanoparticle No. 2 comprises DPPC (Avanti Polar Lipids, Alabaster, AL, United States), cholesterol (SUPELCO, Bellefonte, PA, United States) and DOBA (Sigma, St. Louis, MO, United States) in a molar ratio of 7:2:1, respectively; and
III. Lipid nanoparticle No. 3 comprised DPPC, cholesterol and MPEG-5000-DMPE (Avanti Polar Lipids, Alabaster, AL, United States) in a molar ratio of 4:1:0.125, respectively.

Lipid nanoparticles are manufactured to a mean diameter of approximately 100 nM.

One of the lipid mixtures No. 1-3 is selected. For example, DOPE and MPEG-5000-DMPE are mixed together in the appropriate molar ratios in an organic solvent, such as chloroform. The organic solvent is then evaporated and the dried lipid mixture is re-suspended using vigorous vortexing in a solution comprising phosphate buffered saline, pH 7.4. The re-suspended lipid mixture is then extruded through a 100 nM polycarbonate membrane (T&T Scientific Corporation, Knoxville, TN, United States) equilibrated in phosphate buffered saline to create lipid nanoparticles of an approximate mean diameter of 100 nM. The solution is filter sterilized through 0.2 μM sterile filter (VWR Scientific, Radnor, PA, United States). The mean diameter and size distribution of the lipid nanoparticles is determined by Dynamic Light Scattering (DLS) using a Zetasizer (Malvern Panalytical Ltd, Malvern, United Kingdom), or another suitable technique, known in the art.

Example 3: Composition of the Donor DNA

The donor DNA comprises DNA sequences that are intended to repair a genetic defect. It also comprises DNA sequences which are not found in the target genomic DNA; these sequences do not interfere with the normal gene function but are intended to knockout the I-TevI and or Cas9 sites and/or introduce one or more DNA sequences which are used to track the successful repair of the target gene. Examples of donor DNA include, but are not limited to the following:
I. Linear single-strand DNA of varying lengths comprising homologous regions flanking the sites targeted/cleaved by TevCas9;
II. Linear double-strand DNA of varying lengths comprising homologous regions flanking the sites targeted/cleaved by TevCas9;
III. Double-strand DNA of the same length cleaved by the nuclease and also comprising complimentary DNA ends to those cleaved by TevCas9;
IV. Circular double-strand DNA comprising homologous regions flanking the sites targeted/cleaved by TevCas9; and
V. Circular double-strand DNA comprising an I-TevI target site and Cas9 target site where the product cleaved from the double-strand DNA contains complimentary ends to those cleaved by TevCas9.

Example 4: A Method for Assembling the Lipid-Encapsulated TevCas9 and Transfecting Cells For ex vivo cell transfections: To assemble the lipid-encapsulated TevCas9, a lipid nanoparticle is mixed with the TevCas9 in a 2000:1 molar ratio in Dulbecco's Modified Eagle's Medium (DMEM) (Sigma, St. Louis, MO, United States) and incubated at room temperature for 10 minutes. Cells are transfected with 8.7×10E-17 to 3.1×10E-17 moles of lipid-encapsulated TevCas9 per cell.

For in vivo cell transfection: To assemble the lipid-encapsulated TevCas9, a lipid nanoparticle is mixed with the TevCas9 in a 2000:1 molar ratio in phosphate buffered saline and incubated at room temperature for 10 minutes. The molar ratio of lipid-encapsulated TevCas9 per cell for in vivo transfections is to be determined.

Other Embodiments

The nuclease might contain different combinations of the I-TevI domain, linker domain, Cas9 domain or guide RNA as highlighted below.

Modifications of the I-TevI Domain: Other versions of the I-TevI nuclease domain might contain different combinations of mutations to alter the site targeted by the I-TevI domain or the activity of the I-TevI domain, including mutations that alter the sequence recognized by I-TevI, such as K26 and/or C39. Other versions of the nuclease might substitute the I-TevI domain with other GIY-YIG nuclease domains, such as I-BmoI, Eco29kI, etc. Other versions do not contain Met$^1$ as a result of processing when expressed in E. coli.

Modifications of the Linker Domain: The linker domain might comprise one more of the following to alter binding specificity or activity of TevCas9, including: a). The I-TevI linker domain comprising one or more mutations to amino acid T95, V117, K135, Q158 or N140; b). The linker might contain various combinations of the amino acids shown in SEQ ID NO: 9-12.

Modifications of the Cas9 Domain: Other versions of the Cas9 domain might contain the following: a). A version of the saCas9 domain comprising a D10E mutation (SEQ ID NO:14); b). A version of the saCas9 domain that nicks target DNA on one strand of the target DNA, for example the H557A mutation (SEQ ID NO: 17); c). A version of the saCas9 domain that binds target DNA but does not cleave it, for example mutations at both D10A and H557A mutations (SEQ ID NO: 18); d). A version of the previously described spCas9 EQR mutant comprising the mutations D1135E, R1335Q and T1337R combined with the D10E mutation (SEQ ID NO: 19); and e). A version of the previously described spCas9 EQR mutant comprising the mutations D1135E, R1335Q and T1337R combined with the D10E mutation and a mutation that nicks target DNA on one strand of the target DNA, for example the H840A mutation (SEQ ID NO: 20). Other versions of the saCas9 domain do not contain Met$^1$.

Other versions might substitute other nucleases or DNA binding domains for the Cas9 domain, such as: a). Meganucleases such as the families LAGLIDADG, His-Cys Box, H—N—H, PD-(D/E)xK, Vsr-like, etc.; b). Zinc-finger nucleases; c). Other CRISPR proteins such as scCas9, fnCas9, cjCas9, Cpf1, Cas12a, Cas13a, Cas3, etc.; and d). Other DNA binding domains such as zinc-finger motifs, TALE activator domains, etc.

Modifications of the Guide RNA: a). Other versions of the guide RNA might target the same region of DNA in the CFTR gene or EGFR gene, but contain different sequences to account for genetic polymorphism in populations; b). Other versions of the guide RNA might target different sequences in the CFTR gene or EGFR gene; c). Other version of the guide RNA might target other sequences in a genome to retarget the nuclease to additional clinically relevant targets; d). Other versions of the guide RNA might contain bridged nucleic acids ("BNAs") to enhance target site specificity; and e). Other versions might contain a mixture of guide RNAs to target multiple sequences within the same gene.

Modifications of the Lipid Nanoparticles: a). Other versions of the lipid nanoparticle No. 1, 2 or 3 might have different ratios of each lipid component; b). Other versions of the lipid nanoparticle might have different mean diameters; c). Other versions of the lipid nanoparticle might include different cationic or neutral lipids; d). Other versions of the lipid nanoparticle might include peptides that target specific cell types; e). Other versions of the lipid nanoparticle might include compounds that bind DNA, such as GL67 ($N^4$—Cholesteryl-Spermine); f). the lipid nanoparticle might be lyophilized for enhanced stability; and g). the lipid nanoparticle might be resuspended in a solution other than phosphate buffered saline, such as sterile isotonic saline, water for injection, etc.

Modifications of the Composition of the donor DNA: a). Other version of the linear double-strand donor DNA might contain longer regions of single-strand DNA that is complementary to the target sequence; and b). Other versions of the circular double-strand DNA might contain other DNA sequences intended to increase the rate of homology-directed repair.

Variations to the method of assembling the lipid-encapsulated nuclease and transfecting cells: a). Other versions of the lipid-encapsulated nucleases might contain different molar ratios of lipid nanoparticle to nuclease; b). Media other than DMEM or phosphate buffered saline might be used for the incubation step; c). The nuclease and lipid nanoparticles might be incubated for less or more than 10 minutes; and d). Other molar amounts of nuclease per cell might be used in a transfection reaction.

Variations to the method to manufacture the nuclease: a). Other E. coli expression strains might be used, such as LS5218 (Escherichia coli Genetic Stock Center—Yale University, New Haven, CT, United States) or BL21-DE3 (New England Biolabs, Ipswich, MA, United States) b). Buffer 1 or 2 might contain different concentrations of imidazole, sodium chloride, sodium phosphate (dibasic), or tris hydrochloride and be buffered to a different pH; c). Other processing steps might be used, such as cation or anion exchange chromatography; d). The nuclease might be dialyzed into a solution other than phosphate buffered saline, such as sterile isotonic saline, water for injection, etc.; e). the nuclease might be lyophilized for enhanced stability; f). the guide RNA may be co-expressed from the pACYC-Duet1 expression vector (EMD Millipore, Burlington, MA, United States). The DNA coding sequence of the guide RNA is synthesized (Integrated DNA Technology Inc., Coralville, IA, United States), digested with restrictions endonucleases and inserted into similarly-digested second expression site in the pACYC-Duet1 expression vector; and g). The guide RNA may be synthesized from double-strand DNA by transcribing the guide using the T7 RNA Polymerase HiScribe Kit (New England Biolabs #E2040S, Ipswich, MA, United States) and purifying the guide using an RNA Cleanup Kit (New England Biolabs #T2030L, Ipswich, MA, United States).

Testing

Example 1: A Method to Demonstrate Correction of CFTR Delta F508 and CFTR Protein Functionality in a Model Cell Line A culture of immortalized epithelial cells homozygous for the CFTR delta F508 mutation, such as the CuFi-1 cell line (ATCC® CRL-4013™, American Type Culture Collection, Manassas, VA, United States), is treated with a range of concentrations of lipid-encapsulated TevCas9 and donor DNA (Specific Biologics, Toronto, ON, Canada) in a pharmaceutical formulation targeted to the CFTR delta F508 mutation. An appropriate control cell line, such as NuLi-1 (ATCC® CRL-4011™, American Type Culture Collection, Manassas, VA, United States) immortalized epithelial cells homozygous for wild-type CFTR is also be used.

The proportion of cells with CFTR delta F508 corrected relative to uncorrected cells is measured by the T7 endonuclease I assay (EnGen® Mutation Detection Kit, New England Biolabs #E3321, Ipswich, MA, United States), restriction endonuclease digestion (New England Biolabs, Ipswich, MA, United States) of PCR-amplified target site, deep gene sequencing using an Illumina MiSeq system and barcoded primers flanking the target site (Illumina, San Diego, CA, United States), or other suitable method. The effects of TevCas9 treatment in the control cell line (e.g. NuLi-1 (ATCC® CRL-4011™, American Type Culture Collection, Manassas, VA, United States) is measured. CFTR functionality is measured using short circuit current measurements in an Ussing Camber (Warner Instruments, Hamden, CT, United States) in the presence of a chloride ion gradient in the treated CuFi-1 culture (ATCC® CRL-4013™ American Type Culture Collection, Manassas, VA, United States) versus mock-treated CuFi-1 culture (ATCC® CRL-4013™, American Type Culture Collection, Manassas, VA, United States). The effects of TevCas9 treatment in the control cell line (e.g. NuLi-1) is also measured.

To demonstrate disruption of the EGFR exon 19 deletion mutations(s) and EGFR expression and activity in a model cell line, a culture of immortalized epithelial cells expressing an EGFR exon 19 deletion mutation(s), such as the HCC827 cell line (ATCC® CRL-2868™ American Type Culture Collection, Manassas, VA, United States) is treated with a range of concentrations of lipid-encapsulated TevCas9 (Specific Biologics, Toronto, ON, Canada) in a pharmaceutical formulation of phosphate buffered saline, sterile isotonic saline or water for injection targeted to the EGFR exon 19 deletion. Appropriate control cell lines, such as NuLi-1 (ATCC® CRL-4011™, American Type Culture Collection, Manassas, VA) or immortalized epithelial cell lines homozygous for wild-type EGFR, are used.

The proportion of cells with the EGFR exon 19 deletion disrupted relative to uncorrected cells is measured by the T7 endonuclease I assay (EnGen® Mutation Detection Kit, New England Biolabs #E3321, Ipswich, MA, United States), restriction endonuclease digestion (New England Biolabs, Ipswich, MA, United States) of PCR-amplified target site, deep gene sequencing using an Illumina MiSeq system and barcoded primers flanking the target site (Illumina, San Diego, CA, United States), or other suitable method. The effects of TevCas9 treatment in the control cell line (e.g. NuLi-1 (ATCC® CRL-4011™, American Type Culture Collection, Manassas, VA, United States)) is also measured. EGFR protein expression and activity are measured using an enzyme-linked immunosorbent assay (ELISA) (Sigma, St. Louis, MO, United States) that detects phosphorylated (i.e. activated), unphosphorylated and total EGFR protein in the treated HCC827 culture (ATCC® CRL-2868™, American Type Culture Collection, Manassas, VA, United States) versus mock-treated HCC827 culture. The effects of TevCas9 treatment in the control cell line (e.g. NuLi-1 (ATCC® CRL-4011™, American Type Culture Collection, Manassas, VA, United States)) is also measured.

Example 1: Animal Model Testing Planned to Show Efficacy and Determine Dose-Limiting Toxicity In an example method to demonstrate correction of CFTR delta F508 and/or Cystic Fibrosis symptoms with lipid-encapsulated TevCas9 treatment in an animal model (for example, mouse, rat, minipig or ferret), the lipid-encapsulated TevCas9 in a pharmaceutical formulation of phosphate buffered saline, sterile isotonic saline or water for injection targeted to the CFTR delta F508 is delivered directly to the lungs by either intubation or intranasal delivery. The procedure time is approximately 30-6000 seconds per treatment, depending on the animal model used.

In another method, the lipid-encapsulated TevCas9 in a pharmaceutical formulation targeted to the CFTR delta F508 is nebulized with a commercial nebulizer (Aeroneb®, AeroEclipse®, (Trudell Medical, London, ON, Canada)) or PARI-LC Plus®, (PARI USA, Midlothian, VA, United States)). The average size of the lipid nanoparticle of approximately 100 nM is confirmed post-nebulization by Dynamic Light Scattering (DLS) using a Zetasizer (Malvern Panalytical Ltd, Malvern, United Kingdom), or another suitable technique, known in the art. The composition and concentration of the lipid-encapsulated TevCas9 is confirmed post-nebulization using the MicroGram Lipid Assay Kit (ProFoldin, Hudson, MA, United States) and the presence of an approximately 150 kDa band on a Coomassie-stained SDS-polyacrylamide gel. For measurement of the rate of gene correction, a representative ovine (minipig) animal model (Exemplar Genetics, Sioux City, IA, United States) that is homozygous for the CFTR delta F508 mutation is exposed through the mouth, nose or directly to the lungs with the lipid-encapsulated TevCas9 targeted to CFTR delta F508, as well as a suitable control. General maintenance of these animals includes breeding and farrowing; age-appropriate, bio-secure housing; sound nutrition; basic vaccinations and veterinary care; and documentation consistent with animal welfare guidelines. Maintenance of these animals specific to the CFTR delta F508 may include one of more of the following: surgery to address intestinal obstruction; pancreatic enzyme replacement therapy; vitamins and H2 blockers; and/or proton pump inhibitors to improve gastric acid control. The minipigs are treated with a range of concentrations of lipid-encapsulated TevCas9 that are predicted to be effective from the model cell line studies above for 2 days to 4 weeks for acute toxicity studies and up to 24 months for chronic toxicity studies.

The general health of the animal is monitored post-treatment to assess for any treatment-related adverse events, such as changes in behavior, weight, or food consumption; immune responses; changes to cardiovascular health; mortality, etc. Other efficacy measures post-treatment may include:

I. Forced-expiration, such as forced expiratory volume (or other suitable method) in each animal post-treatment;
II. Overall survival of each animal relative to the control;
III. Other measures of lung function (for example, utilization of mechanical ventilator that can perform general lung function assessments); and
IV. Measurements of the mutation in vivo through tissue sampling and mutation detection methods, such as by polymerase chain reaction.

After the treatment(s) with lipid-encapsulated TevCas9, the animals are sacrificed and the lung and tracheal tissue are harvested.

The proportion of cells with CFTR delta F508 corrected relative to uncorrected cells is measured by the T7 endonuclease I assay (EnGen® Mutation Detection Kit, New England Biolabs #E3321, Ipswich, MA, United States), restriction endonuclease digestion (New England Biolabs, Ipswich, MA, United States) of PCR-amplified target site, deep gene sequencing using an Illumina MiSeq system and barcoded primers flanking the target site (Illumina, San Diego, CA, United States) or other suitable method.

In a method to demonstrate disruption of the EGFR exon 19 deletion mutation(s) and/or Non-small-cell lung cancer (NSCLC) symptoms with TevCas9 treatment in an animal model, the lipid-encapsulated TevCas9 targeted to the EGFR exon 19 deletion mutations in a pharmaceutical formulation of phosphate buffered saline, sterile isotonic saline or water for injection is delivered directly to the lungs through the mouth, nose or directly to the lungs. The procedure time is approximately 30-6000 seconds per treatment, depending on the animal model used.

In another method, the lipid-encapsulated TevCas9 targeted to the EGFR exon 19 deletion mutations in a pharmaceutical formulation is nebulized with a commercial nebulizer ((Aeroneb®, AeroEclipse®, (Trudell Medical, London, ON, Canada) or PARI-LC Plus®, (PARI USA, Midlothian, VA, United States)). The average size of the lipid nanoparticle of approximately 100 nM is confirmed post-nebulization by Dynamic Light Scattering (DLS) using a Zetasizer (Malvern Panalytical Ltd, Malvern, United Kingdom), or another suitable technique, known in the art. The composition and concentration of the lipid-encapsulated TevCas9 nanoparticle is confirmed post-nebulization using the MicroGram Lipid Assay Kit (ProFoldin, Hudson, MA, United States) and the presence of an approximately 150 kDa band on a Coomassie-stained SDS-polyacrylamide gel. For measurement of the rate of gene disruption, a representative murine (mouse) animal model that is homozygous for an EGFR exon 19 deletion mutation(s) is exposed through the nose, mouth or directly to the lungs with the lipid-encapsulated TevCas9 targeted to EGFR exon 19 deletion. The mice are treated with a range of concentrations of TevCas9 that are predicted to be effective from the model cell line studies for 2 days to 4 weeks for acute toxicity studies and up to 24 months for chronic toxicity studies.

The general health of the animal is monitored post-treatment to assess for any treatment-related adverse events, such as changes in behavior, weight, or food consumption; immune responses; changes to cardiovascular health; mortality, etc. Other efficacy measures post-treatment may include:
I. Quantification of EGFR-activating protein through positron emission tomography (PET) with an EGFR mutant tracer;
II. Overall survival of each animal relative to the control(s); and
III. Measures of tumor formation/reduction in each animal over time.

Measurements of the mutation in vivo through tissue sampling and mutation detection methods, such as the Cobas® EGFR mutation test version 2 (Roche Diagnostics, Rischberg, Switzerland). After treatment with nebulized lipid-encapsulated TevCas9, the animals are sacrificed and the lung and tracheal tissue are harvested.

The proportion of cells with the EGFR exon 19 deletion mutation disrupted relative to undisrupted is measured by the T7 endonuclease I assay (EnGen® Mutation Detection Kit, New England Biolabs #E3321, Ipswich, MA, United States), restriction endonuclease digestion (New England Biolabs, Ipswich, MA, United States) of PCR-amplified target site, deep gene sequencing using an Illumina MiSeq system and barcoded primers flanking the target site (Illumina, San Diego, CA, United States) or other suitable method. EGFR protein expression and activity in cells of the harvest tissues are measured using an enzyme-linked immunosorbent assay (ELISA) (Sigma, St. Louis, MO, United States) that detects phosphorylated (i.e. activated), unphosphorylated and total EGFR protein. Determination of dose-limiting toxicity to enable first-in-human clinical studies is based on the predicted effective dose(s) from the animal model studies discussed above, a range of concentrations (in milligrams per kilogram body weight, for example) of lipid-encapsulated TevCas9 is nebulized and delivered to an appropriate animal model for toxicology studies, such as the cynomolgus monkey or other non-human primate. The general health of the animals is monitored for any treatment-related adverse events, such as changes in behavior, weight, or food consumption; immune responses; changes to cardiovascular health; mortality, etc. Other measures of efficacy may be measured in the studies, including those described above.

Therapeutic Effect

The novel chimeric nucleases of the instant invention have been intentionally designed to modify the DNA of lung epithelial cells to treat monogenetic diseases although they are capable of working in other cell types or in the cells of other organisms such as bacteria, yeast, insect, plant or other mammals in vivo or ex vivo to treat monogenetic or polygenetic and infectious diseases.

Example 1: A Method of Targeted Insertion or Replacement of all or a Portion of a DNA Sequence in the Genome of Human Cells FIG. 2A to 2E illustrate the mechanism of action of cellular uptake of the novel chimeric nuclease of the instant invention. As illustrated in FIG. 2A, a cell 20 or cells 20 are exposed to the novel lipid-encapsulated nuclease particles 21 containing the TevCas9 25 either by in vivo or ex vivo administration. As shown in FIG. 2B, the lipid-encapsulated nuclease particle 21 is endocytosed into the cell 20. The endosome 22 goes through a maturation process in the cytosol and is targeted for degradation (FIG. 2C). On certain occasions, the TevCas9 25 can escape the endosome 22 and enter the cytosol (FIG. 2D). In eukaryotic organisms, the nuclease (TevCas9) 25 is targeted to the nucleus 23 of the cell 20 through one or more nuclear-localization sequences ("NLS"). As depicted in FIG. 2E, through its nuclear localization sequence, TevCas9 25 can enter the nucleus 23 and when in the nucleus 23, the TevCas9 nuclease 25 binds to and cleaves 26 the target genomic DNA 24 sequence.

FIG. 3A to 3E illustrate the mechanism of the TevCas9 nuclease in cutting DNA. FIG. 3A is representation of the key features of TevCas9 bound to its target genomic DNA sequence 24 is shown prior to the cleavage reaction. The I-TevI domain 27 targets the I-TevI Target Sequence 29. The linker domain 30 joins the I-TevI domain 27 with the Cas9 domain 28 which targets the Cas9 Target Sequence 31. The gene mutation 32 is surrounded by or in close proximity to the I-TevI Target Sequence 29 and the Cas9 Target Sequence 31. As shown in FIG. 3B, the TevCas9 25 cleaves the target sequence leaving a deletion product 34 of a predictable size with non-complementary DNA ends 35, 36. FIG. 3C illustrates that in the presence of single-stranded donor DNA with homology arms 37, the cell 20 can insert the donor DNA 37 sequence near the cut sites through the homology-directed repair (HDR) pathway 38. FIG. 3D illustrates that in the presence of donor DNA 39 with compatible DNA ends to those cleaved by TevCas9 25, the cell 20 can insert the donor DNA sequence 39 between the cut sites through directed-ligation using the non-homologous end joining (NHEJ) pathway 40. In the absence of donor DNA, the cell 20 can join the DNA ends through the NHEJ pathway 40 (FIG. 3E).

Example 2: The Treatment of Cystic Fibrosis

For the treatment of cystic fibrosis, the exogenous donor DNA contains a DNA sequence, which repairs the CFTR delta F508 mutation involving a method of targeted deletion of a defined length of a DNA sequence in human somatic cells to stimulate homology-directed repair using exogenous donor DNA as a template (FIG. 3C).

Example 3: The Treatment of Non-Small Cell Lung Cancer

For the application of treating non-small cell lung cancer, a version of the Cas9 domain which cuts only one strand of DNA (D10A or H557A mutation) or a nuclease deficient version (the D10A+H557A mutations) is used and the sequences targeted are EGFR exon 19 deletion mutations (SEQ ID NOS: 2-4). In this application, however, the nuclease does not contain exogenous donor DNA. In the absence of exogenous donor DNA, the cell can remove the DNA sequence between the two sites targeted by the nuclease by non-homologous end joining (FIG. 3E).

Alternatively, the inhalation route is a fast and effective way of delivering medication locally to the lungs and for the systemic administration of certain agents. Inhalation drug therapy is used extensively to treat respiratory conditions such as asthma and Chronic Obstructive Pulmonary Disease (COPD). Research is ongoing to develop inhalation systems to treat cystic fibrosis.

The examples which follow are intended in no way to limit the scope of the disclosure but are provided to illustrate how to prepare and use compounds disclosed herein. Many other embodiments of this disclosure will be apparent to one skilled in the art.

A nebulizer is a device that delivers medication to the lungs in the form of an aerosolized vapor. Nebulizers are commonly used to treat respiratory diseases such as asthma and COPD, for example, the nebulization of corticosteroids, although nebulization has also been used for the treatment and prevention of lung infections, such as ARIKAYCE® (Insmed Incorporated, Bridgewater, NJ, United States).

The nebulizer may require some procedure to prepare the liquid for nebulization. The medication is commonly held in liquid form in a cup inside the nebulizer chamber. Once loaded, the device is switched on which generates compressed air to convert the liquid into a vapor in the nebulization chamber. The patient puts the mouthpiece of the nebulization chamber into their mouth and takes a sharp, deep inhalation, holding their breath for 5-10 seconds to ensure the medication reaches the lower parts of the lung. There are a variety of such devices. Many modern nebulizers are breath-actuated and rely on the force of patient inhalation to entrain the aerosolized liquid from the device and thus ensure the medication is delivered only to the patient and not to the surrounding environment. This also ensures consistency of delivering a full dose of the medication to the patient.

The use of nebulizers is well known and nebulizers are commercially available from several sources, such as Aeroneb®, AeroEclipse®, (Trudell Medical, London, ON, Canada) or PARI-LC Plus®, (PARI USA, Midlothian, VA, United States). In an example of the present invention, a nebulizer is utilized for delivery of the lipid-encapsulated novel chimeric nuclease comprising a modified I-TevI nuclease domain, a linker, and a modified RNA-guided nuclease *Staphylococcus aureus* Cas9 of the instant application to the lung epithelial tissue. A sterile liquid version of the therapeutic of interest is loaded into the nebulization chamber and is subsequently aerosolized and is inhaled by the patient into the lung via deep breaths.

Some of the advantages of using a nebulizer versus oral or intravenous administration are: less drug could be required compared to oral or intravenous administration, onset of action can be more rapid via inhalation compared to the oral route, adverse effects are potentially less severe due to local delivery of the medication to the lung tissue where the disease manifests itself, inhaled drug therapy is painless and relatively comfortable for the patient which encourages compliance.

No non-invasive route of delivery provides the speed of action that an inhaled drug can provide. One of the advantages of inhaled drugs is that they are more rapidly absorbed than subcutaneously injected molecules and provides a more immediate physiological response. Small or large molecules, particularly hydrophobic molecules, can be absorbed within seconds after inhalation and can thus be used to treat a wide variety of symptoms that come on suddenly or need long term administration. Pain, panic, anxiety, nausea, cardiovascular crises, bronchoconstriction, sleep induction, spasms, Parkinson's lock-up, and hot flashes are some of the rapid-onset conditions that are addressable with inhaled medicines.

Most protein-based drug products have some water solubility and are rapidly and efficiently absorbed from the lungs. Those that are more hydrophobic are absorbed even more rapidly within seconds to a few minutes. Those that are more hydrophilic are absorbed within minutes to tens of minutes. In one example of the present invention, one vial is aseptically filled with a therapeutic dose of the lipid nanoparticle which is hydrophobic and another vial is aseptically filled with a therapeutic dose of a chimeric nuclease comprising a modified I-TevI nuclease domain, a linker and a modified RNA-guided nuclease *Staphylacoccus aureus* Cas9 which is water soluble and hydrophilic, for delivery to the lungs of a therapeutic dose. The dose can range from 1 to 1000 milligrams of each of the lipid nanoparticle and chimeric nuclease with about 5 to 200 milligrams being preferred. The claimed lipid-encapsulated chimeric nuclease comprising a modified I-TevI nuclease domain, a linker, and a modified RNA-guided nuclease *Staphylacoccus aureus* Cas9 can be absorbed in the cells of the lungs within a few hours and complete cleavage on DNA substrates in vitro has been observed within 2 hours. Other nebulized therapies have been delivered daily. Nebulized administration of the lipid-encapsulated chimeric nuclease, therefore, can be daily or more infrequently depending on its efficacy on a per patient basis. The chimeric nucleases are manufactured by BioVectra Corporation (Charlottetown, PE, Canada) and the vials are aseptically filled by Dalton Pharma Services (Mississauga, ON, Canada). The lipid nanoparticles are manufactured and the vials are aseptically filled by Transferra Nanosciences Inc. (Burnaby, BC, Canada).

The dosage of any disclosed compositions will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions may be readily determined by techniques known to those of skill in the art or as taught herein.

In certain embodiments, the dosage of the subject compounds will generally be in the range of about 1 to 1000 milligrams depending on the body weight of the patient, specifically in the range of about 5 to 200 milligrams.

An effective dose or amount, and any possible effects on the timing of administration of the formulation, may need to be identified for any particular composition of the disclosure. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically re-evaluated to determine the extent of improvement by measuring the same parameters. Adjustments to the amount(s) of subject composition administered and possibly to the time of administration may be made based on these re-evaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions because the onset and duration of effect of the different agents may be complimentary.

Therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of concentrations that include the $ED_{50}$ with little or no toxicity. The dosage may vary within this range depending upon the dosage form employed and the route of administration utilized. For compositions of the disclosure, the therapeutically effective dose may be estimated initially from cell culture assays.

Formulations

Pharmaceutical compositions of the disclosure may be administered by various means, depending on their intended use, as is well known in the art. For example, compositions of the disclosure are to be administered through nebulization. Alternatively, formulations disclosed herein may be administered intravenously, subcutaneously, or intramuscularly. These formulations may be prepared by conventional means, and, if desired, the compositions may be mixed with any conventional additive, such as an excipient, a solubilizing agent, a suspension aid, an emulsifying agent, or preservative agent. The disclosed excipients may serve more than one function. For example, a solubilizing agent may also be a suspension aid, an emulsifier, a preservative, and the like.

The formulations may conveniently be presented in unit dosage form and may be prepared by any methods well known in the art of pharmacy. The amount of a composition that may be combined with a carrier material to produce a single dose vary depending upon the subject being treated, and the particular mode of administration.

Methods of preparing these formulations include the step of bringing into association compositions of the disclosure with the carrier and, optionally, one or more accessory ingredients. In general, the formulations are prepared by uniformly and intimately bringing into association agents with liquid carriers.

It will be appreciated that a disclosed composition may include lyophilized or freeze-dried compounds disclosed herein. For example, disclosed herein are compositions that disclosed compounds crystalline and/or amorphous powder forms. Such forms may be reconstituted for use as e.g., an aqueous composition.

Liquid dosage forms for injection include pharmaceutically acceptable solutions, emulsions, microemulsions, solutions and suspensions. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, glycerol, tetrahydrofuryl alcohol, and fatty acid esters of sorbitan, cyclodextrins, albumin, hyaluronic acid, chitosan and mixtures thereof. Polyethylene glycol (PEG) may be used to obtain desirable properties of solubility, stability, half-life, and other pharmaceutically advantageous properties. Representative examples of stabilizing components include polysorbate 80, L-arginine, polyvinylpyrrolidone, trehalose, and combinations thereof. Other excipients that may be employed, such as solution binders or anti-oxidants include, but are not limited to, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C and xylitol.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

It should be noted that excipients given as examples may have more than one function. For example, a solubilizing agent may also be a suspension aid, an emulsifier, a preservative and the like.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

The compositions of the present invention typically are ready to administer, aqueous solutions which are sterile, storage-stable, and pharmaceutically acceptable without the need for reconstitution prior to administration. The compositions of the present invention are suitable for administration to a subject which means that they are pharmaceutically acceptable, non-toxic, do not contain any components which would adversely affect the biological effects of the chimeric nuclease, and have the pH close to that of the physiological condition which avoids inhalation and/or injection site reactions. The compositions of the present invention do not, for example, comprise any cells.

The compositions are typically stored in a sealed container, vial or cartridge which is typically suitable for long term storage. "Suitable for long-term storage" means that the vial, container or cartridge does not allow for the escape of components of the compositions of the present invention or the ingress of external components, such as, microorganisms when kept for at least 3 months at 25° C.

The compositions of the present invention are preferably administered by nebulization, typically breath-actuated nebulization.

The compositions of the present invention can also be administered by injection as described herein.

The compositions of the present invention may be administered alone or in combination with an additional therapeutic agent, such as an anti-viral, an anti-microbial, a chemotherapeutic and an immunotherapy.

Vials, as used herein, can also comprise two containers one of which contains the chimeric nuclease or lipid particle, as described herein, in a lyophilized powder, as described below, and the second container contains a liquid for reconstitution of the lyophilized powder. The contents of the two containers can be mixed prior to administration.

As discussed above the compositions of the present invention can be administered by nebulization. Suitable volumes of the compositions of the present invention for nebulization include about 0.5 to about 1 ml, about 1 to about 2 ml, about 2 to about 10 ml, or about 10 to about 20 ml.

In the compositions of the present invention the concentration of the chimeric nuclease is from about 0.1 mg/ml to about 10.0 mg/ml, from about 10.0 mg/ml to about 100.0 mg/ml, from about 30.0 mg/ml to about 300.0 mg/ml, from about 500 mg/ml to about 2000 mg/ml and about 2.0 mg/ml.

In the compositions of the present invention the concentration of the lipid nanoparticle is from about 0.1 mg/ml to about 10.0 mg/ml, from about 10.0 mg/ml to about 100.0 mg/ml, from about 30.0 mg/ml to about 300.0 mg/ml, from about 500 mg/ml to about 2000 mg/ml and about 2.0 mg/ml.

We claim:

1. A nuclease comprising a modified *Staphylococcus aureus* Cas9, wherein said modified *Staphylococcus aureus* Cas9 comprises an aspartic acid to glutamic acid substitution at an amino acid corresponding to position 10 of SEQ ID NO: 13, and wherein the amino acid sequence of the *Staphylococcus aureus* Cas9 has at least 99% sequence identity to SEQ ID NO: 13.

2. The nuclease of claim 1, wherein the modified *Staphylococcus aureus* Cas9 comprises a histidine to alanine substitution at an amino acid corresponding to position 557 of SEQ ID NO: 13.

3. The nuclease of claim 1, further comprising an I-TevI nuclease domain.

4. The nuclease of claim 3, wherein the I-TevI nuclease domain comprises the amino acid sequence set forth in SEQ ID NO: 6.

5. The nuclease of claim 3, wherein the I-TevI nuclease domain comprises a substitution or deletion of the methionine at position 1 of SEQ ID NO: 6, and otherwise comprises the amino acid sequence set forth in SEQ ID NO: 6.

6. The nuclease of claim 3, further comprising a linker coupling the modified *Staphylococcus aureus* Cas9 and the I-TevI nuclease domain.

7. The nuclease of claim 6, wherein the linker comprises an amino acid sequence set forth in any one or more of SEQ ID NO: 7 to SEQ ID NO 12.

8. The nuclease of claim 1, bound to a guide RNA.

9. The nuclease of claim 8, wherein the guide RNA comprises one or more bridged nucleic acids.

10. A chimeric nuclease comprising an I-TevI nuclease domain, a linker, a *Staphylococcus aureus* Cas9, and a guide RNA, wherein the *Staphylococcus aureus* Cas9 comprises an aspartic acid to glutamic acid substitution at an amino acid corresponding to position 10 of SEQ ID NO: 13, and wherein the amino acid sequence of the *Staphylococcus aureus* Cas9 has at least 99% sequence identity to SEQ ID NO: 13.

11. The chimeric nuclease of claim 10, wherein the *Staphylococcus aureus* Cas9 comprises a histidine to alanine substitution at an amino acid corresponding to position SS7 of SEQ ID NO: 13.

12. The chimeric nuclease of claim 10, wherein the I-TevI nuclease domain comprises the amino acid sequence set forth in SEQ ID NO: 6.

13. The chimeric nuclease of claim 10, wherein the I-TevI nuclease domain comprises a substitution or deletion of the methionine at position 1 of SEQ ID NO: 6, and otherwise comprises the amino acid sequence set forth in SEQ ID NO: 6.

14. The chimeric nuclease of claim 10, wherein the linker comprises an amino acid sequence set forth in any one or more of SEQ ID NO: 7 to SEQ ID NO 12.

15. A formulation comprising the chimeric nuclease of claim 10 and a lipid nanoparticle.

16. A method to genetically modify the genome of a cell, the method comprising contacting the cell with the chimeric nuclease of claim 11.

17. A nucleic acid encoding the nuclease of claim 1.

18. A nucleic acid encoding the chimeric nuclease of claim 10.

\* \* \* \* \*

SEQUENCE LISTING

```
<160> NUMBER OF SEQ ID NOS: 20

<210> SEQ ID NO 1
<211> LENGTH: 4440
<212> TYPE: DNA
<213> ORGANISM: Homo sapiens

<400> SEQUENCE: 1
atgcagaggt cgcctctgga aaaggccagc gttgtctcca aactttttt cagctggacc      60 agaccaattt tgaggaaagg atacagacag cgcctggaat tgtcagacat ataccaaatc     120
ccttctgttg attctgctga caatctatct gaaaaattgg aaagagaatg ggatagagag     180
ctggcttcaa agaaaaatcc taaactcatt aatgcccttc ggcgatgttt tttctggaga     240
tttatgttct atggaatctt tttatattta ggggaagtca ccaaagcagt acagcctctc     300
ttactgggaa gaatcatagc ttcctatgac ccggataaca aggaggaacg ctctatcgcg     360
atttatctag gcataggctt atgccttctc tttattgtga ggacactgct cctacaccca     420
gccatttttg gccttcatca cattggaatg cagatgagaa tagctatgtt tagtttgatt     480
```

```
tataagaaga ctttaaagct gtcaagccgt gttctagata aaataagtat tggacaactt      540
gttagtctcc tttccaacaa cctgaacaaa tttgatgaag acttgcatt ggcacatttc       600 gtgtggatcg ctcctttgca agtggcactc ctcatggggc taatctggga gttgttacag     660
gcgtctgcct tctgtggact tggtttcctg atagtccttg cccttttca ggctgggcta      720 gggagaatga tgatgaagta cagagatcag agagctggga agatcagtga aagacttgtg    780
attacctcag aaatgattga aaatatccaa tctgttaagg catactgctg ggaagaagca     840
atggaaaaaa tgattgaaaa cttaagacaa acagaactga aactgactcg aaggcagcc     900 tatgtgagat acttcaatag ctcagccttc ttcttctcag ggttctttgt ggtgttttta    960
tctgtgcttc cctatgcact aatcaaagga atcatcctcc ggaaaatatt caccaccatc    1020
tcattctgca ttgttctgcg catggcggtc actcggcaat ttccctgggc tgtacaaaca    1080
tggtatgact ctcttggagc aataaacaaa atacaggatt cttacaaaa gcaagaatat    1140 aagacattgg aatataactt aacgactaca gaagtagtga tggagaatgt aacagccttc   1200
tgggaggagg gatttgggga attatttgag aaagcaaaac aaaacaataa caatagaaaa    1260
acttctaatg gtgatgacag cctcttcttc agtaatttct cacttcttgg tactcctgtc    1320
ctgaaagata ttaatttcaa gatagaaaga ggacagttgt tggcggttgc tggatccact    1380
ggagcaggca agacttcact tctaatggtg attatgggag aactggagcc ttcagagggt    1440
aaaattaagc acagtggaag aatttcattc tgttctcagt tttcctggat tatgcctggc    1500
accattaaag aaaatatcat tggtgtttcc tatgatgaat atagatacag aagcgtcatc    1560
aaagcatgcc aactagaaga ggacatctcc aagtttgcag agaaagacaa tatagttctt    1620
ggagaaggtg gaatcacact gagtggaggt caacgagcaa gaatttcttt agcaagagca    1680
gtatacaaag atgctgattt gtatttatta gactctcctt ttggataccct agatgtttta    1740 acagaaaaag aaatatttga aagctgtgtc tgtaaactga tggctaacaa aactaggatt    1800
ttggtcactt ctaaaatgga acatttaaag aaagctgaca aaatattaat tttgcatgaa    1860
ggtagcagct atttttatgg gacattttca gaactccaaa atctacagcc agactttagc    1920
tcaaaactca tgggatgtga ttctttcgac caatttagtg cagaaagaag aaattcaatc    1980
ctaactgaga ccttacaccg tttctcatta gaaggagatg ctcctgtctc ctggacagaa    2040
acaaaaaaac aatcttttaa acagactgga gagtttgggg aaaaaaggaa gaattctatt    2100
ctcaatccaa tcaactctat acgaaaattt tccattgtgc aaaagactcc cttacaaatg    2160
aatggcatcg aagaggattc tgatgagcct ttagagagaa ggctgtcctt agtaccagat    2220
tctgagcagg gagaggcgat actgcctcgc atcagcgtga tcagcactgg ccccacgctt    2280
caggcacgaa ggaggcagtc tgtcctgaac ctgatgacac actcagttaa ccaaggtcag    2340
aacattcacc gaaagacaac agcatccaca cgaaaagtgt cactggcccc tcaggcaaac    2400
ttgactgaac tggatatata ttcaagaagg ttatctcaag aaactggctt ggaaataagt    2460
gaagaaatta cgaagaaga cttaaaggag tgctttttg atgatatgga gagcatacca    2520
gcagtgacta catggaacac ataccttcga tatattactg tccacaagag cttaattttt    2580
gtgctaattt ggtgcttagt aattttttctg gcagaggtgg ctgcttcttt ggttgtgctg    2640
tggctccttg aaacactcc tcttcaagac aaagggaata gtactcatag tagaaataac    2700
agctatgcag tgattatcac cagcaccagt tcgtattatg tgttttacat ttacgtggga    2760
gtagccgaca ctttgcttgc tatgggattc ttcagaggtc taccactggt gcatactcta    2820
atcacagtgt cgaaaatttt acaccacaaa atgttacatt ctgttcttca agcacctatg    2880
```

```
tcaaccctca acacgttgaa agcaggtggg attcttaata gattctccaa agatatagca    2940
attttggatg accttctgcc tcttaccata tttgacttca tccagttgtt attaattgtg    3000
attggagcta tagcagttgt cgcagtttta caaccctaca tctttgttgc aacagtgcca    3060
gtgatagtgg cttttattat gttgagagca tatttcctcc aaacctcaca gcaactcaaa    3120
caactggaat ctgaaggcag gagtccaatt ttcactcatc ttgttacaag cttaaaagga    3180
ctatggacac ttcgtgcctt cggacggcag ccttactttg aaactctgtt ccacaaagct    3240
ctgaatttac atactgccaa ctggttcttg tacctgtcaa cactgcgctg gttccaaatg    3300
agaatagaaa tgattttgt catcttcttc attgctgtta ccttcatttc cattttaaca    3360
acaggagaag gagaaggaag agttggtatt atcctgactt tagccatgaa tatcatgagt    3420
acattgcagt gggctgtaaa ctccagcata gatgtggata gcttgatgcg atctgtgagc    3480
cgagtcttta agttcattga catgccaaca gaaggtaaac ctaccaagtc aaccaaacca    3540
tacaagaatg gccaactctc gaaagttatg attattgaga attcacacgt gaagaaagat    3600
gacatctggc cctcaggggg ccaaatgact gtcaaagatc tcacagcaaa atacacagaa    3660 ggtgaaatg ccatattaga gaacatttcc ttctcaataa gtcctggcca gagggtgggc    3720
ctcttgggaa gaactggatc agggaagagt actttgttat cagctttttt gagactactg    3780
aacactgaag gagaaatcca gatcgatggt gtgtcttggg attcaataac tttgcaacag    3840
tggaggaaag cctttggagt gataccacag aaagtattta ttttttctgg aacatttaga    3900
aaaaacttgg atccctatga acagtggagt gatcaagaaa tatggaaagt tgcagatgag    3960
gttgggctca gatctgtgat agaacagttt cctgggaagc ttgactttgt ccttgtggat    4020
gggggctgtg tcctaagcca tggccacaag cagttgatgt gcttggctag atctgttctc    4080
agtaaggcga agatcttgct gcttgatgaa cccagtgctc atttggatcc agtaacatac    4140
caaataatta gaagaactct aaaacaagca tttgctgatt gcacagtaat tctctgtgaa    4200
cacaggatag aagcaatgct ggaatgccaa cattttttgg tcatagaaga gaacaaagtg    4260
cggcagtacg attccatcca gaaactgctg aacgagagga gcctcttccg gcaagccatc    4320
agcccctccg acagggtgaa gctctttccc caccggaact caagcaagtg caagtctaag    4380
ccccagattg ctgctctgaa agaggagaca gaagaagagg tgcaagatac aaggctttag    4440
```

<210> SEQ ID NO 2
<211> LENGTH: 3261
<212> TYPE: DNA
<213> ORGANISM: Homo sapiens

<400> SEQUENCE: 2

```
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
cagggacaaa agtgtgatcc aagctgtccc aatgggagct gctggggtgc aggagaggag     480
aactgccaga aactgaccaa aatcatctgt gcccagcagt gctccgggcg ctgccgtggc     540
```

```
aagtccccca gtgactgctg ccacaaccag tgtgctgcag gctgcacagg cccccgggag    600
agcgactgcc tggtctgccg caaattccga gacgaagcca cgtgcaagga cacctgcccc    660
ccactcatgc tctacaaccc caccacgtac cagatggatg tgaaccccga gggcaaatac    720
agctttggtg ccacctgcgt gaagaagtgt ccccgtaatt atgtggtgac agatcacggc    780
tcgtgcgtcc gagcctgtgg ggccgacagc tatgagatgg aggaagacgg cgtccgcaag    840
tgtaagaagt gcgaagggcc ttgccgcaaa gtgtgtaacg gaataggtat tggtgaattt    900
aaagactcac tctccataaa tgctacgaat attaaacact tcaaaaactg cacctccatc    960
agtggcgatc tccacatcct gccggtggca tttaggggtg actccttcac acatactcct   1020
cctctggatc cacaggaact ggatattctg aaaaccgtaa aggaaatcac agggttttg    1080 ctgattcagg cttggcctga aaacaggacg gacctccatg cctttgagaa cctagaaatc   1140
atacgcggca ggaccaagca acatggtcag ttttctcttg cagtcgtcag cctgaacata   1200
acatccttgg gattacgctc cctcaaggag ataagtgatg gagatgtgat aatttcagga   1260
aacaaaaatt tgtgctatgc aaatacaata aactggaaaa aactgtttgg gacctccggt   1320
cagaaaacca aaattataag caacagaggt gaaaacagct gcaaggccac aggccaggtc   1380
tgccatgcct tgtgctcccc cgagggctgc tggggcccgg agcccaggga ctgcgtctct   1440
tgccggaatg tcagccgagg cagggaatgc gtggacaagt gcaaccttct ggagggtgag   1500
ccaagggagt ttgtggagaa ctctgagtgc atacagtgcc acccagagtg cctgcctcag   1560
gccatgaaca tcacctgcac aggacgggga ccagacaact gtatccagtg tgcccactac   1620
attgacggcc cccactgcgt caagacctgc ccggcaggag tcatgggaga aaacaacacc   1680
ctggtctgga gtacgcaga cgccggccat gtgtgccacc tgtgccatcc aaactgcacc   1740 tacgatgca ctgggccagg tcttgaaggc tgtccaacga atgggcctaa gatcccgtcc   1800
atcgccactg ggatggtggg ggccctcctc ttgctgctgg tggtggccct ggggatcggc   1860
ctcttcatgc gaaggcgcca catcgttcgg aagcgcacgc tgcggaggct gctgcaggag   1920
agggagcttg tggagcctct tacacccagt ggagaagctc ccaaccaagc tctcttgagg   1980
atcttgaagg aaactgaatt caaaaagatc aaagtgctgg gctccggtgc gttcggcacg   2040
gtgtataagg gactctggat cccagaaggt gagaaagtta aaattcccgt cgctatcaaa   2100
acatctccga agccaacaa ggaaatcctc gatgaagcct acgtgatggc cagcgtggac   2160 aaccccacg tgtgccgcct gctgggcatc tgcctcacct ccaccgtgca gctcatcacg   2220
cagctcatgc ccttcggctg cctcctggac tatgtccggg aacacaaaga caatattggc   2280
tcccagtacc tgctcaactg gtgtgtgcag atcgcaaagg gcatgaacta cttggaggac   2340
cgtcgcttgg tgcaccgcga cctggcagcc aggaacgtac tggtgaaaac accgcagcat   2400
gtcaagatca cagattttgg gctggccaaa ctgctgggtg cggaagagaa agaataccat   2460
gcagaaggag gcaaagtgcc tatcaagtgg atggcattgg aatcaatttt acacagaatc   2520
tatacccacc agagtgatgt ctggagctac ggggtgaccg tttgggagtt gatgacctt    2580 ggatccaagc catatgacgg aatccctgcc agcgagatct cctccatcct ggagaaagga   2640
gaacgcctcc ctcagccacc catatgtacc atcgatgtct acatgatcat ggtcaagtgc   2700
tggatgatag acgcagatag tcgcccaaag ttccgtgagt tgatcatcga attctccaaa   2760
atggcccgag accccagcg ctaccttgtc attcaggggg atgaaagaat gcatttgcca   2820
agtcctacag actccaactt ctaccgtgcc ctgatggatg aagaagacat ggacgacgtg   2880
gtggatgccg acgagtacct catcccacag cagggcttct tcagcagccc ctccacgtca   2940
```

| | |
|---|---|
| cggactcccc tcctgagctc tctgagtgca accagcaaca attccaccgt ggcttgcatt | 3000 |
| gatagaaatg ggctgcaaag ctgtcccatc aaggaagaca gcttcttgca gcgatacagc | 3060 |
| tcagacccca caggcgcctt gactgaggac agcatagacg acaccttcct cccagtgcct | 3120 |
| ggtgagtggc ttgtctggaa acagtcctgc tcctcaacct cctcgaccca ctcagcagca | 3180 |
| gccagtctcc agtgtccaag ccaggtgctc cctccagcat ctccagaggg ggaaacagtg | 3240 |
| gcagatttgc agacacagtg a | 3261 |

<210> SEQ ID NO 3
<211> LENGTH: 3260
<212> TYPE: DNA
<213> ORGANISM: Homo sapiens

<400> SEQUENCE: 3

| | |
|---|---|
| atgcgaccct ccgggacggc cggggcagcg ctcctggcgc tgctggctgc gctctgcccg | 60 |
| gcgagtcggg ctctgaggaa aaagaaagtt tgccaaggca cgagtaacaa gctcacgcag | 120 |
| ttgggcactt ttgaagatca ttttctcagc ctccagagga tgttcaataa ctgtgaggtg | 180 |
| gtccttggga atttgaaaat tacctatgtg cagaggaatt atgatctttc cttcttaaag | 240 |
| accatccagg aggtggctgg ttatgtcctc attgccctca acacagtgga gcgaattcct | 300 |
| ttggaaaacc tgcagatcat cagaggaaat atgtactacg aaaattccta tgccttagca | 360 |
| gtcttatcta actatgatgc aaataaaacc ggactgaagg agctgcccat gagaaattta | 420 |
| cagggacaaa agtgtgatcc aagctgtccc aatgggagct gctggggtgc aggagaggag | 480 |
| aactgccaga aactgaccaa atcatctgt gcccagcagt gctccgggcg ctgccgtggc | 540 |
| aagtccccca gtgactgctg ccacaaccag tgtgctgcag gctgcacagg cccccgggag | 600 |
| agcgactgcc tggtctgccg caaattccga gacgaagcca cgtgcaagga cacctgcccc | 660 |
| ccactcatgc tctacaaccc caccacgtac cagatggatg tgaaccccga gggcaaatac | 720 |
| agctttggtg ccacctgcgt gaagaagtgt ccccgtaatt atgtggtgac agatcacggc | 780 |
| tcgtgcgtcc gagcctgtgg ggccgacagc tatgagatgg aggaagacgg cgtccgcaag | 840 |
| tgtaagaagt gcgaagggcc ttgccgcaaa gtgtgtaacg gaataggtat tggtgaattt | 900 |
| aaagactcac tctccataaa tgctacgaat attaaacact tcaaaaactg cacctccatc | 960 |
| agtggcgatc tccacatcct gccggtggca tttaggggtg actccttcac acatactcct | 1020 |
| cctctggatc cacaggaact ggatattctg aaaaccgtaa aggaaatcac agggtttttg | 1080 |
| ctgattcagg cttggcctga aacaggacg gacctccatg cctttgagaa cctagaaatc | 1140 |
| atacgcggca ggaccaagca acatggtcag ttttctcttg cagtcgtcag cctgaacata | 1200 |
| acatccttgg gattacgctc cctcaaggag ataagtgatg gagatgtgat aatttcagga | 1260 |
| aacaaaaatt tgtgctatgc aaatacaata aactggaaaa aactgtttgg gacctccggt | 1320 |
| cagaaaacca aaattataag caacagaggt gaaaacagct gcaaggccac aggccaggtc | 1380 |
| tgccatgcct tgtgctcccc cgagggctgc tggggcccgg agcccaggga ctgcgtctct | 1440 |
| tgccggaatg tcagccgagg cagggaatgc gtggacaagt gcaaccttct ggagggtgag | 1500 |
| ccaagggagt ttgtggagaa ctctgagtgc atacagtgcc acccagagtg cctgcctcag | 1560 |
| gccatgaaca tcacctgcac aggacgggga ccagacaact gtatccagtg tgcccactac | 1620 |
| attgacggcc ccactgcgt caagacctgc ccggcaggag tcatgggaga aaacaacacc | 1680 |
| ctggtctgga agtacgcaga cgccggccat gtgtgccacc tgtgccatcc aaactgcacc | 1740 |

```
tacggatgca ctgggccagg tcttgaaggc tgtccaacga atgggcctaa gatcccgtcc    1800
atcgccactg ggatggtggg ggccctcctc ttgctgctgg tggtggccct ggggatcggc    1860
ctcttcatgc gaaggcgcca catcgttcgg aagcgcacgc tgcggaggct gctgcaggag    1920
agggagcttg tggagcctct tacacccagt ggagaagctc ccaaccaagc tctcttgagg    1980
atcttgaagg aaactgaatt caaaaagatc aaagtgctgg gctccggtgc gttcggcacg    2040
gtgtataagg gactctggat cccagaaggt gagaaagtta aaattcccgt cgctatcaag    2100
acatctccga aagccaacaa ggaaatcctc gatgagccta cgtgatggcc agcgtggaca    2160 accccccacgt gtgccgcctg ctgggcatct gcctcacctc caccgtgcag ctcatcacgc    2220
agctcatgcc cttcggctgc ctcctggact atgtccggga cacaaagac aatattggct    2280 cccagtacct gctcaactgg tgtgtgcaga tcgcaaaggg catgaactac ttggaggacc    2340
gtcgcttggt gcaccgcgac ctggcagcca ggaacgtact ggtgaaaaca ccgcagcatg    2400
tcaagatcac agattttggg ctggccaaac tgctgggtgc ggaagagaaa gaataccatg    2460
cagaaggagg caaagtgcct atcaagtgga tggcattgga atcaatttta cacagaatct    2520
atacccacca gagtgatgtc tggagctacg gggtgaccgt ttgggagttg atgaccttg    2580 gatccaagcc atatgacgga atccctgcca gcgagatctc ctccatcctg gagaaaggag    2640
aacgcctccc tcagccaccc atatgtacca tcgatgtcta catgatcatg gtcaagtgct    2700
ggatgataga cgcagatagt cgcccaaagt tccgtgagtt gatcatcgaa ttctccaaaa    2760
tggcccgaga ccccagcgc taccttgtca ttcaggggga tgaagaatg catttgccaa    2820 gtcctacaga ctccaacttc taccgtgccc tgatggatga agaagacatg gacgacgtgg    2880
tggatgccga cgagtacctc atcccacagc agggcttctt cagcagcccc tccacgtcac    2940
ggactcccct cctgagctct ctgagtgcaa ccagcaacaa ttccaccgtg gcttgcattg    3000
atagaaatgg gctgcaaagc tgtcccatca aggaagacag cttcttgcag cgatacagct    3060
cagaccccac aggcgccttg actgaggaca gcatagacga caccttcctc ccagtgcctg    3120
gtgagtggct tgtctggaaa cagtcctgct cctcaacctc ctcgacccac tcagcagcag    3180
ccagtctcca gtgtccaagc caggtgctcc ctccagcatc tccagagggg gaaacagtgg    3240
cagatttgca gacacagtga                                                3260
```

```
<210> SEQ ID NO 4
<211> LENGTH: 3259
<212> TYPE: DNA
<213> ORGANISM: Homo sapiens

<400> SEQUENCE: 4
```

```
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
cagggacaaa agtgtgatcc aagctgtccc aatgggagct gctggggtgc aggagaggag     480
aactgccaga aactgaccaa aatcatctgt gcccagcagt gctccgggcg ctgccgtggc     540 aagtcccca gtgactgctg ccacaaccag tgtgctgcag gctgcacagg cccccgggag     600
```

```
agcgactgcc tggtctgccg caaattccga gacgaagcca cgtgcaagga cacctgcccc   660
ccactcatgc tctacaaccc caccacgtac cagatggatg tgaaccccga gggcaaatac   720
agctttggtg ccacctgcgt gaagaagtgt ccccgtaatt atgtggtgac agatcacggc   780
tcgtgcgtcc gagcctgtgg ggccgacagc tatgagatgg aggaagacgg cgtccgcaag   840
tgtaagaagt gcgaagggcc ttgccgcaaa gtgtgtaacg gataggtat tggtgaattt   900
aaagactcac tctccataaa tgctacgaat attaaacact tcaaaaactg cacctccatc   960
agtggcgatc tccacatcct gccggtggca tttaggggtg actccttcac acatactcct  1020
cctctggatc cacaggaact ggatattctg aaaaccgtaa aggaaatcac agggttttg   1080
ctgattcagg cttggcctga aaacaggacg gacctccatg cctttgagaa cctagaaatc  1140
atacgcggca ggaccaagca acatggtcag ttttctcttg cagtcgtcag cctgaacata  1200
acatccttgg gattacgctc cctcaaggag ataagtgatg gagatgtgat aatttcagga  1260
aacaaaaatt tgtgctatgc aaatacaata aactggaaaa aactgtttgg gacctccggt  1320
cagaaaacca aaattataag caacagaggt gaaaacagct gcaaggccac aggccaggtc  1380
tgccatgcct tgtgctcccc cgagggctgc tggggcccgg agcccaggga ctgcgtctct  1440
tgccggaatg tcagccgagg cagggaatgc gtggacaagt gcaaccttct ggagggtgag  1500
ccaagggagt ttgtggagaa ctctgagtgc atacagtgcc acccagagtg cctgcctcag  1560
gccatgaaca tcacctgcac aggacgggga ccagacaact gtatccagtg tgcccactac  1620
attgacggcc cccactgcgt caagacctgc ccggcaggag tcatgggaga aaacaacacc  1680
ctggtctgga agtacgcaga cgccggccat gtgtgccacc tgtgccatcc aaactgcacc  1740
tacggatgca ctgggccagg tcttgaaggc tgtccaacga atgggcctaa gatcccgtcc  1800
atcgccactg ggatggtggg ggccctcctc ttgctgctgg tggtgccct ggggatcggc  1860
ctcttcatgc gaaggcgcca catcgttcgg aagcgcacgc tgcggaggct gctgcaggag  1920
agggagcttg tggagcctct tacacccagt ggagaagctc ccaaccaagc tctcttgagg  1980
atcttgaagg aaactgaatt caaaaagatc aaagtgctgg gctccggtgc gttcggcacg  2040
gtgtataagg gactctggat cccagaaggt gagaaagtta aaattcccgt cgctatcaag  2100
catctccgaa agccaacaag gaaatcctcg atgagcctac gtgatggcca gcgtggacaa  2160
cccccacgtg tgccgcctgc tgggcatctg cctcacctcc accgtgcagc tcatcacgca  2220
gctcatgccc ttcggctgcc tcctggacta tgtccgggaa cacaaagaca atattggctc  2280
ccagtacctg ctcaactggt gtgtgcagat cgcaaagggc atgaactact ggaggaccg  2340
tcgcttggtg caccgcgacc tggcagccag gaacgtactg gtgaaaacac cgcagcatgt  2400
caagatcaca gattttgggc tggccaaact gctgggtgcg aagagaaag aataccatgc  2460
agaaggaggc aaagtgccta tcaagtggat ggcattggaa tcaattttac acagaatcta  2520
tacccaccag agtgatgtct ggagctacgg ggtgaccgtt tggagttga tgacctttgg  2580
atccaagcca tatgacggaa tccctgccag cgagatctcc tccatcctgg agaaaggaga  2640
acgcctccct cagccaccca tatgtaccat cgatgtctac atgatcatgg tcaagtgctg  2700
gatgatagac gcagatagtc gcccaaagtt ccgtgagttg atcatcgaat ctccaaaat  2760
ggcccgagac ccccagcgct accttgtcat tcaggggat gaaagaatgc atttgccaag  2820
tcctacagac tccaacttct accgtgccct gatggatgaa gaagacatgg acgacgtggt  2880
ggatgccgac gagtacctca tcccacagca gggcttcttc agcagcccct ccacgtcacg  2940
```

| | |
|---|---:|
| gactcccctc ctgagctctc tgagtgcaac cagcaacaat tccaccgtgg cttgcattga | 3000 |
| tagaaatggg ctgcaaagct gtcccatcaa ggaagacagc ttcttgcagc gatacagctc | 3060 |
| agaccccaca ggcgccttga ctgaggacag catagacgac accttcctcc cagtgcctgg | 3120 |
| tgagtggctt gtctggaaac agtcctgctc ctcaacctcc tcgacccact cagcagcagc | 3180 |
| cagtctccag tgtccaagcc aggtgctccc tccagcatct cagaggggga aaacagtggc | 3240 |
| agatttgcag acacagtga | 3259 |

```
<210> SEQ ID NO 5
<211> LENGTH: 3276
<212> TYPE: DNA
<213> ORGANISM: Homo sapiens

<400> SEQUENCE: 5
```

| | |
|---|---:|
| atgcgaccct ccgggacggc cggggcagcg ctcctggcgc tgctggctgc gctctgcccg | 60 |
| gcgagtcggg ctctggagga aaagaaagtt tgccaaggca cgagtaacaa gctcacgcag | 120 |
| ttgggcactt ttgaagatca tttctcagc ctccagagga tgttcaataa ctgtgaggtg | 180 |
| gtccttggga atttggaaat tacctatgtg cagaggaatt atgatctttc cttcttaaag | 240 |
| accatccagg aggtggctgg ttatgtcctc attgccctca acacagtgga gcgaattcct | 300 |
| ttggaaaacc tgcagatcat cagaggaaat atgtactacg aaaattccta tgccttagca | 360 |
| gtcttatcta actatgatgc aaataaaacc ggactgaagg agctgcccat gagaaattta | 420 |
| cagggacaaa agtgtgatcc aagctgtccc aatgggagct gctggggtgc aggagaggag | 480 |
| aactgccaga aactgaccaa atcatctgt gcccagcagt gctccgggcg ctgccgtggc | 540 |
| aagtccccca gtgactgctg ccacaaccag tgtgctgcag gctgcacagg ccccgggag | 600 |
| agcgactgcc tggtctgccg caaattccga gacgaagcca cgtgcaagga cacctgcccc | 660 |
| ccactcatgc tctacaaccc caccacgtac cagatggatg tgaaccccga gggcaaatac | 720 |
| agctttggtg ccacctgcgt gaagaagtgt ccccgtaatt atgtggtgac agatcacggc | 780 |
| tcgtgcgtcc gagcctgtgg ggccgacagc tatgagatgg aggaagacgg cgtccgcaag | 840 |
| tgtaagaagt gcgaagggcc ttgccgcaaa gtgtgtaacg gaataggtat tggtgaattt | 900 |
| aaagactcac tctccataaa tgctacgaat attaaacact tcaaaaactg cacctccatc | 960 |
| agtggcgatc tccacatcct gccggtggca tttaggggtg actccttcac acatactcct | 1020 |
| cctctggatc cacaggaact ggatattctg aaaaccgtaa aggaaatcac agggttttg | 1080 |
| ctgattcagg cttggcctga aacaggacg gacctccatg cctttgagaa cctagaaatc | 1140 |
| atacgcggca ggaccaagca acatggtcag ttttctcttg cagtcgtcag cctgaacata | 1200 |
| acatccttgg gattacgctc cctcaaggag ataagtgatg gagatgtgat aatttcagga | 1260 |
| aacaaaaatt tgtgctatgc aaatacaata aactggaaaa actgtttgg gacctccggt | 1320 |
| cagaaaacca aaattataag caacagaggt gaaaacagct gcaaggccac aggccaggtc | 1380 |
| tgccatgcct tgtgctcccc cgagggctgc tggggcccgg agcccaggga ctgcgtctct | 1440 |
| tgccggaatg tcagccgagg cagggaatgc gtggacaagt gcaaccttct ggagggtgag | 1500 |
| ccaagggagt ttgtggagaa ctctgagtgc atacagtgcc acccagagtg cctgcctcag | 1560 |
| gccatgaaca tcacctgcac aggacgggga ccagacaact gtatccagtg cccactac | 1620 |
| attgacggcc ccactgcgt caagacctgc ccggcaggag tcatgggaga aaacaacacc | 1680 |
| ctggtctgga agtacgcaga cgccggccat gtgtgccacc tgtgccatcc aaactgcacc | 1740 |
| tacggatgca ctgggccagg tcttgaaggc tgtccaacga atgggcctaa gatcccgtcc | 1800 |

```
atcgccactg ggatggtggg ggccctcctc ttgctgctgg tggtggccct ggggatcggc    1860
ctcttcatgc gaaggcgcca catcgttcgg aagcgcacgc tgcggaggct gctgcaggag    1920
agggagcttg tggagcctct tacacccagt ggagaagctc ccaaccaagc tctcttgagg    1980
atcttgaagg aaactgaatt caaaaagatc aaagtgctgg gctccggtgc gttcggcacg    2040
gtgtataagg gactctggat cccagaaggt gagaaagtta aaattcccgt cgctatcaag    2100
gaattaagag aagcaacatc tccgaaagcc aacaaggaaa tcctcgatga agcctacgtg    2160
atggccagcg tggacaaccc ccacgtgtgc cgcctgctgg gcatctgcct cacctccacc    2220
gtgcagctca tcacgcagct catgcccttc ggctgcctcc tggactatgt ccgggaacac    2280
aaagacaata ttggctccca gtacctgctc aactggtgtg tgcagatcgc aaagggcatg    2340
aactacttgg aggaccgtcg cttggtgcac cgcgacctgg cagccaggaa cgtactggtg    2400
aaaacaccgc agcatgtcaa gatcacagat tttgggctgg ccaaactgct gggtgcggaa    2460
gagaaagaat accatgcaga aggaggcaaa gtgcctatca gtggatggca ttggaatca    2520 attttacaca gaatctatac ccaccagagt gatgtctgga gctacggggt gaccgtttgg    2580
gagttgatga cctttggatc caagccatat gacggaatcc ctgccagcga gatctcctcc    2640
atcctggaga aggagaacg cctccctcag ccacccatat gtaccatcga tgtctacatg    2700
atcatggtca gtgctggat gatagacgca gatagtcgcc caaagttccg tgagttgatc    2760
atcgaattct ccaaaatggc ccgagacccc cagcgctacc ttgtcattca ggggatgaa    2820 agaatgcatt tgccaagtcc tacagactcc aacttctacc gtgccctgat ggatgaagaa    2880
gacatggacg acgtggtgga tgccgacgag tacctcatcc cacagcaggg cttcttcagc    2940
agcccctcca cgtcacggac tccccctcctg agctctctga gtgcaaccag caacaattcc    3000
accgtggctt gcattgatag aaatgggctg caaagctgtc ccatcaagga agacagcttc    3060
ttgcagcgat acagctcaga ccccacaggc gccttgactg aggacagcat agacgacacc    3120
ttcctcccag tgcctggtga gtggcttgtc tggaaacagt cctgctcctc aacctcctcg    3180
acccactcag cagcagccag tctccagtgt ccaagccagg tgctccctcc agcatctcca    3240
gagggggaaa cagtggcaga tttgcagaca cagtga                             3276
```

<210> SEQ ID NO 6
<211> LENGTH: 93
<212> TYPE: PRT
<213> ORGANISM: Enterobacteria Phage T4

<400> SEQUENCE: 6

```
Met Gly Lys Ser Gly Ile Tyr Gln Ile Lys Asn Thr Leu Asn Asn Lys
1               5                   10                  15

Val Tyr Val Gly Ser Ala Lys Asp Phe Glu Lys Arg Trp Lys Arg His
                20                  25                  30

Phe Lys Asp Leu Glu Lys Gly Cys His Ser Ser Ile Lys Leu Gln Arg
            35                  40                  45

Ser Phe Asn Lys His Gly Asn Val Phe Glu Cys Ser Ile Leu Glu Glu
        50                  55                  60

Ile Pro Tyr Glu Lys Asp Leu Ile Ile Glu Arg Glu Asn Phe Trp Ile
65                  70                  75                  80

Lys Glu Leu Asn Ser Lys Ile Asn Gly Tyr Asn Ile Ala
                85                  90
```

<210> SEQ ID NO 7

```
<211> LENGTH: 83
<212> TYPE: PRT
<213> ORGANISM: Artificial Sequence
<220> FEATURE:
<223> OTHER INFORMATION: V117F Mutated Linker

<400> SEQUENCE: 7

Asp Ala Thr Phe Gly Asp Thr Cys Ser Thr His Pro Leu Lys Glu Glu
1               5                   10                  15

Ile Ile Lys Lys Arg Ser Glu Thr Phe Lys Ala Lys Met Leu Lys Leu
            20                  25                  30

Gly Pro Asp Gly Arg Lys Ala Leu Tyr Ser Lys Pro Gly Ser Lys Asn
        35                  40                  45

Gly Arg Trp Asn Pro Glu Thr His Lys Phe Cys Lys Cys Gly Val Arg
    50                  55                  60

Ile Gln Thr Ser Ala Tyr Thr Cys Ser Lys Cys Arg Asn Gly Gly Ser
65                  70                  75                  80

Gly Gly Ser

<210> SEQ ID NO 8
<211> LENGTH: 83
<212> TYPE: PRT
<213> ORGANISM: Artificial Sequence
<220> FEATURE:
<223> OTHER INFORMATION: V117F K135R N140S Mutated Linker

<400> SEQUENCE: 8

Asp Ala Thr Phe Gly Asp Thr Cys Ser Thr His Pro Leu Lys Glu Glu
1               5                   10                  15

Ile Ile Lys Lys Arg Ser Glu Thr Val Lys Ala Lys Met Leu Lys Leu
            20                  25                  30

Gly Pro Asp Gly Arg Lys Ala Leu Tyr Ser Arg Pro Gly Ser Lys Ser
        35                  40                  45

Gly Arg Trp Asn Pro Glu Thr His Lys Phe Cys Lys Cys Gly Val Arg
    50                  55                  60

Ile Gln Thr Ser Ala Tyr Thr Cys Ser Lys Cys Arg Asn Gly Gly Ser
65                  70                  75                  80

Gly Gly Ser

<210> SEQ ID NO 9
<211> LENGTH: 83
<212> TYPE: PRT
<213> ORGANISM: Artificial Sequence
<220> FEATURE:
<223> OTHER INFORMATION: Linker Domain Variant

<400> SEQUENCE: 9

Asp Ala Thr Phe Gly Asp Thr Cys Ser Thr His Pro Leu Lys Glu Glu
1               5                   10                  15

Ile Ile Lys Lys Arg Ser Glu Thr Phe Lys Ala Lys Met Leu Lys Leu
            20                  25                  30

Gly Pro Asp Gly Arg Lys Ala Leu Tyr Ser Arg Pro Gly Ser Lys Ser
        35                  40                  45

Gly Arg Trp Asn Pro Glu Thr His Lys Phe Cys Lys Cys Gly Val Arg
    50                  55                  60

Ile Gln Thr Ser Ala Tyr Thr Cys Ser Lys Cys Arg Asn Gly Gly Ser
65                  70                  75                  80

Gly Gly Ser
```

```
<210> SEQ ID NO 10
<211> LENGTH: 86
<212> TYPE: PRT
<213> ORGANISM: Artificial Sequence
<220> FEATURE:
<223> OTHER INFORMATION: Linker Domain Variant

<400> SEQUENCE: 10

Asp Ala Thr Phe Gly Asp Thr Cys Ser Thr His Pro Leu Lys Glu Glu
1               5                   10                  15

Ile Ile Lys Lys Arg Ser Glu Thr Val Lys Ala Lys Met Leu Lys Leu
                20                  25                  30

Gly Pro Asp Gly Arg Lys Ala Leu Tyr Ser Arg Pro Gly Ser Lys Ser
            35                  40                  45

Gly Arg Trp Asn Pro Glu Thr His Lys Phe Cys Lys Cys Gly Val Arg
    50                  55                  60

Ile Gln Thr Ser Ala Tyr Thr Cys Ser Lys Cys Arg Asn Gly Gly Ser
65                  70                  75                  80

Gly Gly Thr Gly Gly Ser
                85

<210> SEQ ID NO 11
<211> LENGTH: 87
<212> TYPE: PRT
<213> ORGANISM: Artificial Sequence
<220> FEATURE:
<223> OTHER INFORMATION: Linker Domain Variant

<400> SEQUENCE: 11

Asp Ala Thr Phe Gly Asp Thr Cys Ser Thr His Pro Leu Lys Glu Glu
1               5                   10                  15

Ile Ile Lys Lys Arg Ser Glu Thr Val Lys Ala Lys Met Leu Lys Leu
                20                  25                  30

Gly Pro Asp Gly Arg Lys Ala Leu Tyr Ser Arg Pro Gly Ser Lys Ser
            35                  40                  45

Gly Arg Trp Asn Pro Glu Thr His Lys Phe Cys Lys Cys Gly Val Arg
    50                  55                  60

Ile Gln Thr Ser Ala Tyr Thr Cys Ser Lys Cys Arg Asn Gly Gly Gly
65                  70                  75                  80

Gly Ser Gly Gly Gly Gly Ser
                85

<210> SEQ ID NO 12
<211> LENGTH: 95
<212> TYPE: PRT
<213> ORGANISM: Artificial Sequence
<220> FEATURE:
<223> OTHER INFORMATION: Linker Domain Variant

<400> SEQUENCE: 12

Asp Ala Thr Phe Gly Asp Thr Cys Ser Thr His Pro Leu Lys Glu Glu
1               5                   10                  15

Ile Ile Lys Lys Arg Ser Glu Thr Val Lys Ala Lys Met Leu Lys Leu
                20                  25                  30

Gly Pro Asp Gly Arg Lys Ala Leu Tyr Ser Arg Pro Gly Ser Lys Ser
            35                  40                  45

Gly Arg Trp Asn Pro Glu Thr His Lys Phe Cys Lys Cys Gly Val Arg
    50                  55                  60

Ile Gln Thr Ser Ala Tyr Thr Cys Ser Lys Cys Arg Asn Lys Glu Ser
```

-continued

```
                65                  70                  75                  80
Gly Ser Val Ser Ser Glu Gln Leu Ala Gln Phe Arg Ser Leu Asp
                    85                  90                  95

<210> SEQ ID NO 13
<211> LENGTH: 1053
<212> TYPE: PRT
<213> ORGANISM: Staphylococcus aureus

<400> SEQUENCE: 13

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg Arg His Arg Ile
        50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350
```

```
Lys Ile Leu Thr Ile Tyr Gln Ser Glu Asp Ile Gln Glu Leu
            355                 360                 365

Thr Asn Leu Asn Ser Glu Leu Thr Gln Glu Glu Ile Glu Gln Ile Ser
370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
            435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Arg Thr Thr
                500                 505                 510

Gly Lys Glu Asn Ala Lys Tyr Leu Ile Glu Lys Ile Lys Leu His Asp
            515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
            595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
```

```
                770             775             780
Asn Asp Thr Leu Tyr Ser Thr Arg Lys Asp Asp Lys Gly Asn Thr Leu
785             790             795             800

Ile Val Asn Asn Leu Asn Gly Leu Tyr Asp Lys Asp Asn Asp Lys Leu
                805             810             815

Lys Lys Leu Ile Asn Lys Ser Pro Glu Lys Leu Leu Met Tyr His His
                820             825             830

Asp Pro Gln Thr Tyr Gln Lys Leu Lys Leu Ile Met Glu Gln Tyr Gly
                835             840             845

Asp Glu Lys Asn Pro Leu Tyr Lys Tyr Glu Glu Thr Gly Asn Tyr
850             855             860

Leu Thr Lys Tyr Ser Lys Lys Asp Asn Gly Pro Val Ile Lys Lys Ile
865             870             875             880

Lys Tyr Tyr Gly Asn Lys Leu Asn Ala His Leu Asp Ile Thr Asp Asp
                885             890             895

Tyr Pro Asn Ser Arg Asn Lys Val Val Lys Leu Ser Leu Lys Pro Tyr
                900             905             910

Arg Phe Asp Val Tyr Leu Asp Asn Gly Val Tyr Lys Phe Val Thr Val
                915             920             925

Lys Asn Leu Asp Val Ile Lys Lys Glu Asn Tyr Tyr Glu Val Asn Ser
930             935             940

Lys Cys Tyr Glu Glu Ala Lys Lys Leu Lys Lys Ile Ser Asn Gln Ala
945             950             955             960

Glu Phe Ile Ala Ser Phe Tyr Asn Asn Asp Leu Ile Lys Ile Asn Gly
                965             970             975

Glu Leu Tyr Arg Val Ile Gly Val Asn Asn Asp Leu Leu Asn Arg Ile
                980             985             990

Glu Val Asn Met Ile Asp Ile Thr Tyr Arg Glu Tyr Leu Glu Asn Met
                995             1000            1005

Asn Asp Lys Arg Pro Pro Arg Ile Ile Lys Thr Ile Ala Ser Lys
            1010            1015            1020

Thr Gln Ser Ile Lys Lys Tyr Ser Thr Asp Ile Leu Gly Asn Leu
            1025            1030            1035

Tyr Glu Val Lys Ser Lys Lys His Pro Gln Ile Ile Lys Lys Gly
            1040            1045            1050
```

<210> SEQ ID NO 14
<211> LENGTH: 1053
<212> TYPE: PRT
<213> ORGANISM: Artificial Sequence
<220> FEATURE:
<223> OTHER INFORMATION: SACAS9 D10E Mutant

<400> SEQUENCE: 14

```
Met Lys Arg Asn Tyr Ile Leu Gly Leu Glu Ile Gly Ile Thr Ser Val
1               5               10              15

Gly Tyr Gly Ile Ile Asp Tyr Glu Thr Arg Asp Val Ile Asp Ala Gly
                20              25              30

Val Arg Leu Phe Lys Glu Ala Asn Val Glu Asn Asn Glu Gly Arg Arg
            35              40              45

Ser Lys Arg Gly Ala Arg Arg Leu Lys Arg Arg Arg His Arg Ile
    50              55              60

Gln Arg Val Lys Lys Leu Leu Phe Asp Tyr Asn Leu Leu Thr Asp His
65              70              75              80

Ser Glu Leu Ser Gly Ile Asn Pro Tyr Glu Ala Arg Val Lys Gly Leu
```

```
                    85                  90                  95
Ser Gln Lys Leu Ser Glu Glu Phe Ser Ala Ala Leu Leu His Leu
                100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
        130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510
```

```
Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925
```

```
Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 15
<211> LENGTH: 21
<212> TYPE: RNA
<213> ORGANISM: Artificial Sequence
<220> FEATURE:
<223> OTHER INFORMATION: Targets CFTR Gene

<400> SEQUENCE: 15
gcgucaucaa agcaugccaa c                                              21

<210> SEQ ID NO 16
<211> LENGTH: 22
<212> TYPE: RNA
<213> ORGANISM: Artificial Sequence
<220> FEATURE:
<223> OTHER INFORMATION: Targets EGFR Gene

<400> SEQUENCE: 16
aagccaacaa ggaaauccuc ga                                             22

<210> SEQ ID NO 17
<211> LENGTH: 1053
<212> TYPE: PRT
<213> ORGANISM: Artificial Sequence
<220> FEATURE:
<223> OTHER INFORMATION: SACAS9 D10E + H557A Mutant

<400> SEQUENCE: 17

Met Lys Arg Asn Tyr Ile Leu Gly Leu Glu Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110
```

-continued

```
Ala Lys Arg Arg Gly Val His Asn Val Asn Glu Val Glu Glu Asp Thr
            115                 120                 125
Gly Asn Glu Leu Ser Thr Lys Glu Gln Ile Ser Arg Asn Ser Lys Ala
    130                 135                 140
Leu Glu Glu Lys Tyr Val Ala Glu Leu Gln Leu Glu Arg Leu Lys Lys
145                 150                 155                 160
Asp Gly Glu Val Arg Gly Ser Ile Asn Arg Phe Lys Thr Ser Asp Tyr
                    165                 170                 175
Val Lys Glu Ala Lys Gln Leu Leu Lys Val Gln Lys Ala Tyr His Gln
                180                 185                 190
Leu Asp Gln Ser Phe Ile Asp Thr Tyr Ile Asp Leu Leu Glu Thr Arg
            195                 200                 205
Arg Thr Tyr Tyr Glu Gly Pro Gly Glu Gly Ser Pro Phe Gly Trp Lys
        210                 215                 220
Asp Ile Lys Glu Trp Tyr Glu Met Leu Met Gly His Cys Thr Tyr Phe
225                 230                 235                 240
Pro Glu Glu Leu Arg Ser Val Lys Tyr Ala Tyr Asn Ala Asp Leu Tyr
                    245                 250                 255
Asn Ala Leu Asn Asp Leu Asn Asn Leu Val Ile Thr Arg Asp Glu Asn
                260                 265                 270
Glu Lys Leu Glu Tyr Tyr Glu Lys Phe Gln Ile Ile Glu Asn Val Phe
            275                 280                 285
Lys Gln Lys Lys Lys Pro Thr Leu Lys Gln Ile Ala Lys Glu Ile Leu
        290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                    325                 330                 335
Ala Arg Lys Glu Ile Ile Glu Asn Ala Glu Leu Leu Asp Gln Ile Ala
                340                 345                 350
Lys Ile Leu Thr Ile Tyr Gln Ser Ser Glu Asp Ile Gln Glu Glu Leu
            355                 360                 365
Thr Asn Leu Asn Ser Glu Leu Thr Gln Glu Glu Ile Glu Gln Ile Ser
        370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                    405                 410                 415
Ile Phe Asn Arg Leu Lys Leu Val Pro Lys Lys Val Asp Leu Ser Gln
                420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
        450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                    485                 490                 495
Arg Asn Arg Gln Thr Asn Glu Arg Ile Glu Ile Ile Arg Thr Thr
                500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
```

-continued

```
                530                 535                 540
Asp Leu Leu Asn Asn Pro Phe Asn Tyr Glu Val Asp Ala Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
                610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
                675                 680                 685

Lys Phe Lys Lys Glu Arg Asn Lys Gly Tyr Lys His His Ala Glu Asp
                690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
                770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
                835                 840                 845

Asp Glu Lys Asn Pro Leu Tyr Lys Tyr Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
                915                 920                 925

Lys Asn Leu Asp Val Ile Lys Lys Glu Asn Tyr Tyr Glu Val Asn Ser
                930                 935                 940

Lys Cys Tyr Glu Glu Ala Lys Lys Leu Lys Lys Ile Ser Asn Gln Ala
945                 950                 955                 960
```

```
Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
                980                 985                 990

Glu Val Asn Met Ile Asp Ile Thr Tyr Arg Glu Tyr Leu Glu Asn Met
                995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 18
<211> LENGTH: 1053
<212> TYPE: PRT
<213> ORGANISM: Artificial Sequence
<220> FEATURE:
<223> OTHER INFORMATION: SACAS9 D10A + H557A Mutant

<400> SEQUENCE: 18

Met Lys Arg Asn Tyr Ile Leu Gly Leu Ala Ile Gly Ile Thr Ser Val
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
                100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
                180                 185                 190

Leu Asp Gln Ser Phe Ile Asp Thr Tyr Ile Asp Leu Leu Glu Thr Arg
            195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270
```

```
Glu Lys Leu Glu Tyr Tyr Glu Lys Phe Gln Ile Ile Glu Asn Val Phe
            275                 280                 285
Lys Gln Lys Lys Lys Pro Thr Leu Lys Gln Ile Ala Lys Glu Ile Leu
        290                 295                 300
Val Asn Glu Glu Asp Ile Lys Gly Tyr Arg Val Thr Ser Thr Gly Lys
305                 310                 315                 320
Pro Glu Phe Thr Asn Leu Lys Val Tyr His Asp Ile Lys Asp Ile Thr
                    325                 330                 335
Ala Arg Lys Glu Ile Ile Glu Asn Ala Glu Leu Leu Asp Gln Ile Ala
                340                 345                 350
Lys Ile Leu Thr Ile Tyr Gln Ser Ser Glu Asp Ile Gln Glu Glu Leu
            355                 360                 365
Thr Asn Leu Asn Ser Glu Leu Thr Gln Glu Glu Ile Glu Gln Ile Ser
        370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                    405                 410                 415
Ile Phe Asn Arg Leu Lys Leu Val Pro Lys Lys Val Asp Leu Ser Gln
                420                 425                 430
Gln Lys Glu Ile Pro Thr Thr Leu Val Asp Asp Phe Ile Leu Ser Pro
            435                 440                 445
Val Val Lys Arg Ser Phe Ile Gln Ser Ile Lys Val Ile Asn Ala Ile
        450                 455                 460
Ile Lys Lys Tyr Gly Leu Pro Asn Asp Ile Ile Glu Leu Ala Arg
465                 470                 475                 480
Glu Lys Asn Ser Lys Asp Ala Gln Lys Met Ile Asn Glu Met Gln Lys
                    485                 490                 495
Arg Asn Arg Gln Thr Asn Glu Arg Ile Glu Glu Ile Arg Thr Thr
                500                 505                 510
Gly Lys Glu Asn Ala Lys Tyr Leu Ile Glu Lys Ile Lys Leu His Asp
            515                 520                 525
Met Gln Glu Gly Lys Cys Leu Tyr Ser Leu Glu Ala Ile Pro Leu Glu
        530                 535                 540
Asp Leu Leu Asn Asn Pro Phe Asn Tyr Glu Val Asp Ala Ile Ile Pro
545                 550                 555                 560
Arg Ser Val Ser Phe Asp Asn Ser Phe Asn Asn Lys Val Leu Val Lys
                    565                 570                 575
Gln Glu Glu Asn Ser Lys Lys Gly Asn Arg Thr Pro Phe Gln Tyr Leu
                580                 585                 590
Ser Ser Ser Asp Ser Lys Ile Ser Tyr Glu Thr Phe Lys Lys His Ile
            595                 600                 605
Leu Asn Leu Ala Lys Gly Lys Gly Arg Ile Ser Lys Thr Lys Lys Glu
        610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
                    645                 650                 655
Met Asn Leu Leu Arg Ser Tyr Phe Arg Val Asn Asn Leu Asp Val Lys
                660                 665                 670
Val Lys Ser Ile Asn Gly Gly Phe Thr Ser Phe Leu Arg Arg Lys Trp
            675                 680                 685
```

```
Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
            725                 730                 735

Gln Ala Glu Ser Met Pro Glu Ile Glu Thr Glu Gln Glu Tyr Lys Glu
        740                 745                 750

Ile Phe Ile Thr Pro His Gln Ile Lys His Ile Lys Asp Phe Lys Asp
    755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr Tyr Arg Glu Tyr Leu Glu Asn Met
        995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 19
<211> LENGTH: 1368
<212> TYPE: PRT
<213> ORGANISM: Artificial Sequence
<220> FEATURE:
<223> OTHER INFORMATION: SPCAS9 D10E, D1135E, R1335Q, T1337R Mutant

<400> SEQUENCE: 19
```

-continued

```
Met Asp Lys Lys Tyr Ser Ile Gly Leu Glu Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
            50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
```

```
                420             425             430
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845
```

```
Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Glu Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

Phe Glu Lys Asn Pro Ile Asp Phe Leu Glu Ala Lys Gly Tyr Lys
    1175            1180            1185

Glu Val Lys Lys Asp Leu Ile Ile Lys Leu Pro Lys Tyr Ser Leu
    1190            1195            1200

Phe Glu Leu Glu Asn Gly Arg Lys Arg Met Leu Ala Ser Ala Gly
    1205            1210            1215

Glu Leu Gln Lys Gly Asn Glu Leu Ala Leu Pro Ser Lys Tyr Val
    1220            1225            1230

Asn Phe Leu Tyr Leu Ala Ser His Tyr Glu Lys Leu Lys Gly Ser
    1235            1240            1245
```

```
Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Gln Tyr Arg Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 20
<211> LENGTH: 1368
<212> TYPE: PRT
<213> ORGANISM: Artificial Sequence
<220> FEATURE:
<223> OTHER INFORMATION: SPCAS9 D10E, H840A, D1135E, R1335Q, T1337R
      Mutant

<400> SEQUENCE: 20

Met Asp Lys Lys Tyr Ser Ile Gly Leu Glu Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240
```

-continued

```
Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655
```

-continued

Thr Gly Trp Gly Arg Leu Ser Arg Lys Leu Ile Asn Gly Ile Arg Asp
          660                 665                 670

Lys Gln Ser Gly Lys Thr Ile Leu Asp Phe Leu Lys Ser Asp Gly Phe
          675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
              725                 730                 735

Ile Leu Gln Thr Val Lys Val Val Asp Glu Leu Val Lys Val Met Gly
              740                 745                 750

Arg His Lys Pro Glu Asn Ile Val Ile Glu Met Ala Arg Glu Asn Gln
              755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
              805                 810                 815

Gln Asn Gly Arg Asp Met Tyr Val Asp Gln Glu Leu Asp Ile Asn Arg
              820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
              885                 890                 895

Phe Asp Asn Leu Thr Lys Ala Glu Arg Gly Gly Leu Ser Glu Leu Asp
              900                 905                 910

Lys Ala Gly Phe Ile Lys Arg Gln Leu Val Glu Thr Arg Gln Ile Thr
              915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
              965                 970                 975

Glu Ile Asn Asn Tyr His His Ala His Asp Ala Tyr Leu Asn Ala Val
              980                 985                 990

Val Gly Thr Ala Leu Ile Lys Lys Tyr Pro Lys Leu Glu Ser Glu Phe
              995                1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val

-continued

```
                1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Glu Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Gln Tyr Arg Ser
    1325                1330                1335
Thr Lys Glu Val Leu Asp Ala Thr Leu Ile His Gln Ser Ile Thr
    1340                1345                1350
Gly Leu Tyr Glu Thr Arg Ile Asp Leu Ser Gln Leu Gly Gly Asp
    1355                1360                1365
```